US006989075B1

(12) United States Patent
Kao et al.

(10) Patent No.: US 6,989,075 B1
(45) Date of Patent: Jan. 24, 2006

(54) TENSION ACTIVATABLE SUBSTRATE

(75) Inventors: Junan Kao, Cincinnati, OH (US); Michelle Renee Gannon, Cincinnati, OH (US); Michael Gomer Stelljes, Jr., West Chester, OH (US); Paul Dennis Trokhan, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 738 days.

(21) Appl. No.: 09/715,354

(22) Filed: Nov. 17, 2000

Related U.S. Application Data

(63) Continuation-in-part of application No. 09/705,616, filed on Nov. 3, 2000, now abandoned.

(51) Int. Cl.
*D21H 11/00* (2006.01)
*D21H 13/00* (2006.01)

(52) U.S. Cl. .................................. 162/125; 162/123

(58) Field of Classification Search ............... 162/109, 162/113, 114, 116, 194
See application file for complete search history.

(56) References Cited

U.S. PATENT DOCUMENTS

| 1,384,515 | A | * | 7/1921 | Conradson et al. ......... 162/114 |
| 2,113,431 | A | * | 4/1938 | Milliken ..................... 162/114 |
| 2,130,375 | A | * | 9/1938 | Atkins ........................ 162/114 |
| 2,281,945 | A | * | 5/1942 | Milliken ..................... 162/114 |
| 2,950,223 | A | * | 8/1960 | Bletzinger et al. .......... 162/114 |
| 3,034,180 | A | * | 5/1962 | Greiner et al. .............. 162/114 |
| 3,081,514 | A | * | 3/1963 | Griswold .................... 162/114 |
| 3,301,746 | A | | 1/1967 | Sanford et al. ............. 162/113 |
| 3,650,877 | A | | 3/1972 | Johnson ....................... 161/47 |
| 3,756,907 | A | * | 9/1973 | Heling ........................ 162/114 |
| 3,823,887 | A | | 7/1974 | Gerstein ..................... 242/56.2 |
| 3,852,152 | A | | 12/1974 | Werner et al. .............. 161/168 |
| 3,855,053 | A | | 12/1974 | Fuss .......................... 161/168 |

(Continued)

FOREIGN PATENT DOCUMENTS

| GB | 423828 | * | 2/1935 | ................. 162/114 |

(Continued)

OTHER PUBLICATIONS

U.S. Appl. No. 09/318,676, filed May 25, 1999, McAtee et al.

*Primary Examiner*—Dionne A. Walls
*Assistant Examiner*—Lisa L. Herring
(74) *Attorney, Agent, or Firm*—Peter D. Meyer; David K. Mattheis; Julia A. Glazer

(57) ABSTRACT

A dual intensive property tissue. The tissue has a first set of intensive properties including density, surface area, thickness and void volume as presented to the consumer. The consumer plastically activates the tissue by pulling it in tension. A series of slits 44 or other lines of weakness elongate in a direction parallel to the line of tension, allowing the tissue to achieve a second state of intensive properties. The value of the second state of intensive properties is different after activation. The change in value of the intensive properties allows for economies in shipping, where a higher density product is shipped to the consumer. At the point of use, the consumer activates the product to achieve the increase surface area and lower density. The increase in surface area and concomitant decrease in density provides for increased efficacy in cleaning. The plastically activatable state may be provided by a series of slits 44 or other lines of weakness in the tissue. The tissue may comprise cellulosic and/or synthetic fibers. The tissue may be used as a facial tissue, bath tissue, paper towel, napkin, body wipe, mop-head, etc.

21 Claims, 31 Drawing Sheets

U.S. PATENT DOCUMENTS

| | | | |
|---|---|---|---|
| 3,856,615 A | 12/1974 | Dreher | 161/168 |
| 3,895,128 A | 7/1975 | Gaiser | 428/43 |
| 3,944,694 A | 3/1976 | McQueary | |
| 3,956,556 A | 5/1976 | McQueary | 428/131 |
| 3,975,564 A | 8/1976 | Jones | 428/174 |
| 3,994,771 A * | 11/1976 | Morgan et al. | 162/113 |
| 4,025,996 A | 5/1977 | Saveker | 428/594 |
| 4,097,983 A | 7/1978 | Cole | 29/521 |
| 4,144,624 A | 3/1979 | Szego et al. | |
| 4,177,897 A | 12/1979 | Cole | 206/389 |
| 4,191,609 A | 3/1980 | Trokhan | 162/113 |
| 4,237,776 A | 12/1980 | Ottaviano | 493/382 |
| 4,247,289 A | 1/1981 | McCabe | 493/386 |
| 4,500,586 A | 2/1985 | Bussey, Jr. | 428/174 |
| 4,529,480 A | 7/1985 | Trokhan | 162/109 |
| 4,557,716 A | 12/1985 | Ottaviano | 493/464 |
| 4,606,965 A | 8/1986 | Bussey | 428/158 |
| 4,615,671 A | 10/1986 | Bernal | 425/289 |
| 4,636,417 A | 1/1987 | Rasmussen | 428/91 |
| 4,637,859 A | 1/1987 | Trokhan | 162/109 |
| 4,650,456 A | 3/1987 | Armington | 493/464 |
| 4,717,613 A | 1/1988 | Ottaviano | 428/129 |
| 4,750,896 A | 6/1988 | Komaransky et al. | 493/357 |
| 4,935,282 A | 6/1990 | Pawlowski et al. | 428/121 |
| 4,992,324 A | 2/1991 | Dube | 428/226 |
| 5,134,013 A | 7/1992 | Parker | 428/182 |
| 5,151,312 A | 9/1992 | Boeri | 428/156 |
| 5,164,045 A | 11/1992 | Awofeso et al. | |
| 5,173,352 A | 12/1992 | Parker | 428/174 |
| 5,188,581 A | 2/1993 | Baldacci | 493/381 |
| 5,194,315 A | 3/1993 | Itoh | 428/178 |
| 5,196,254 A | 3/1993 | Akiyama | 428/178 |
| 5,198,276 A | 3/1993 | Nakajima | 428/43 |
| 5,203,761 A | 4/1993 | Reichental et al. | 493/346 |
| 5,254,389 A | 10/1993 | Tether | 428/131 |
| 5,277,761 A * | 1/1994 | Van Phan | 162/116 |
| 5,322,168 A | 6/1994 | Kataoka | 206/588 |
| 5,330,819 A | 7/1994 | Krueger | 428/102 |
| 5,340,638 A | 8/1994 | Sperner | 428/182 |
| 5,364,504 A | 11/1994 | Smurkoski et al. | 162/116 |
| 5,365,819 A | 11/1994 | Maida et al. | 83/332 |
| 5,374,381 A | 12/1994 | Schuld et al. | 261/106 |
| 5,503,715 A * | 4/1996 | Trokhan et al. | 162/113 |
| 5,529,664 A | 6/1996 | Trokhan et al. | 162/109 |
| 5,593,755 A | 1/1997 | Fuss | 428/134 |
| 5,595,811 A | 1/1997 | Stout, Jr. | 428/181 |
| 5,628,876 A * | 5/1997 | Ayers et al. | 162/358.2 |
| 5,650,384 A | 7/1997 | Gordon et al. | 510/159 |
| 5,652,035 A | 7/1997 | Tseng | 428/43 |
| 5,667,871 A | 9/1997 | Goodrich et al. | 428/136 |
| 5,674,344 A | 10/1997 | Thompson et al. | 156/250 |
| 5,679,222 A | 10/1997 | Rasch et al. | 162/358.1 |
| 5,688,578 A | 11/1997 | Goodrich | 428/136 |
| 5,712,020 A | 1/1998 | Parker | 428/182 |
| 5,714,041 A | 2/1998 | Ayers et al. | 162/111 |
| 5,733,403 A | 3/1998 | Morley | 156/207 |
| 5,744,213 A | 4/1998 | Nelson | 428/131 |
| 5,782,735 A | 7/1998 | Goodrich et al. | 493/338 |
| 5,789,050 A | 8/1998 | Kang | |
| 5,861,081 A * | 1/1999 | Bredendick et al. | 162/114 |
| 5,895,627 A | 4/1999 | Khachatoorian | 422/58 |
| D409,343 S | 5/1999 | Kingry et al. | |
| 5,906,710 A | 5/1999 | Trokhan | 162/109 |
| 5,910,079 A | 6/1999 | Watanabe | 493/352 |
| 5,910,089 A | 6/1999 | Weder | 53/472 |
| 5,932,068 A | 8/1999 | Farrington, Jr. et al. | 162/117 |
| 6,067,779 A | 5/2000 | Weder | 53/472 |
| 6,080,459 A | 6/2000 | Keller | |
| 6,101,661 A | 8/2000 | Policicchio et al. | 15/228 |
| 6,180,214 B1 | 1/2001 | Nissing et al. | |
| 6,203,663 B1 * | 3/2001 | Kamps et al. | 162/113 |

FOREIGN PATENT DOCUMENTS

| | | |
|---|---|---|
| WO | WO 98/52458 | 11/1988 |
| WO | WO 98/11813 | 3/1998 |
| WO | WO 98/15262 | 4/1998 |
| WO | WO 99/06793 | 2/1999 |
| WO | WO 99/07273 | 2/1999 |
| WO | WO 99/37200 | 7/1999 |
| WO | WO 99/37476 | 7/1999 |
| WO | WO 99/37747 | 7/1999 |
| WO | WO 99/25318 | 5/2000 |
| WO | PCT/US00/34746 | 12/2000 |
| WO | WO 01/12902 A1 | 2/2001 |

\* cited by examiner

TENSION ACTIVATABLE SUBSTRATE

CROSS REFERENCE TO RELATED APPLICATION

This application is a continuation-in-part of prior application entitled "Tension Activatable Substrate", filed on Nov. 3, 2000 in the name of Junan Kao et al. Ser. No. 09/705,616 now abandoned.

FIELD OF INVENTION

This invention relates to flexible substrates user activatable from a first state of intensive properties to a second state of intensive properties.

BACKGROUND OF THE INVENTION

Nonwoven substrates, particularly tissue papers, are well known in the art. Tissue papers are commonly used as facial tissues, bath tissue, paper towels, napkins and wipes. More recently, synthetic nonwovens have been used in the shower as poofs for washing one's skin and as a disposable mophead for cleaning floors and other hard surfaces. Suitable body wash implements are disclosed in commonly assigned U.S. Pat. No. 5,650,384, issued Jul. 22, 1997 to Gordon et al., and commonly assigned Pat. Apps. WO 98/15262, WO 99/25318, WO 99/06793, all of which are incorporated herein by reference. Exemplary mops having disposable nonwoven substrates are illustrated by commonly assigned U.S. Pat. No. 6,101,661, issued Aug. 15, 2000 to Polieicchio et al., and U.S. Pat. No. Des. 409,343, issued May 4, 1999 to Kingry et al., both incorporated herein by reference, and by the mops marketed by the instant assignee as Swifter mops. Discrete apertured nonwoven substrates are also illustrated in commonly assigned U.S. Pat. No. 5,895,627, issued Apr. 20, 1999 to Trokhan, and incorporated herein by reference. Commonly assigned WO 98/11813, published Mar. 26, 1998 in the name of Sherry and incorporated herein by reference, discloses a cleaning implement having a wettable cleaning pad.

It has long been a goal in the art of making tissue paper to make tissue paper having lower density, also known as having higher bulk. One of the first attempts in the art to improve tissue by lowering the density is found in commonly assigned U.S. Pat. No. 3,301,746, issued Jan. 31, 1967 to Sanford et al. and incorporated herein by reference. Sanford et al. discloses through air dried paper having substantially lower overall density than that of conventional press felt dried tissue. U.S. Pat. No. 4,191,609, issued Mar. 4, 1980 to Trokhan, and incorporated herein by reference, discloses an improvement to low density, through air dried paper. This patent discloses paper made with a pattern of biaxially staggered low density zones which provides increased flexibility.

Yet another series of commonly assigned patents illustrate low density papermaking through the use of belts having photosensitive resin. This technology provided flexibility to the papermaking process which was previously unavailable. Exemplary patents showing such technology include commonly assigned U.S. Pat. No. 4,529,480, issued Jul. 16, 1985 to Trokhan; U.S. Pat. No. 4,637,859, issued Jan. 20, 1987 to Trokhan; U.S. Pat. No. 5,364,504, issued Nov. 15, 1994 to Smurkoski et al.; U.S. Pat. No. 5,529,664, issued Jun. 25, 1996 to Trokhan et al.; U.S. Pat. No. 5,679,222 issued Oct. 21, 1997 to Rasch et al.; U.S. Pat. No. 5,714,041 issued Feb. 3, 1998 to Ayers et al.; and U.S. Pat. No. 5,906,710, issued May 25, 1999 to Trokhan, and incorporated herein by reference.

Yet another technology purportedly achieving low density tissue is found in U.S. Pat. No. 5,932,068, issued Aug. 3, 1999 to Farrington, Jr. et al. This patent purports to make low density tissue without creping.

However, each of the aforementioned disclosures of tissue paper present a tissue paper to the user having only a single set of intensive properties. Intensive properties include but are not limited to density, thickness, coefficient of friction, volume (on a unit area basis), surface area (on a unit area basis) and void volume.

More particularly, the tissue paper of the prior art has only a single overall or bulk density. The user cannot significantly affect the density of the tissue paper once the manufacturing process is complete. However, there are times the user may desire tissue paper to be of a different density than that which is initially presented at the point of purchase. For example, the user may desire a higher density tissue paper for shipping and storage and a lower density tissue paper for the ultimate use. If so, it would be convenient for the consumer to have a sheet of tissue paper presented with a first density and transformable into a second and substantially lesser density.

Likewise, the user may desire the tissue paper to be transformed from a first volume to a second volume and/or thickness. The second volume and/or thickness may be greater than the first. The increase in volume and/or thickness may provide the benefit of a first and lesser volume and/or thickness for shipment and storage prior to the point of use by the consumer. At the point of use, the consumer may activate the tissue paper to a second and greater volume and/or thickness. Such increased volume and/or thickness provides the benefit, for example, the increased volume and/or thickness would provide hand protection for the user during use. This can be particularly advantageous when the product is used as a bath tissue or for cleaning other surfaces.

Likewise, the user is typically not able to significantly modify the surface area of the tissue paper once the manufacturing process is complete. As used herein, the term "surface area" refers to the amount of surface area, considering the topography, of the tissue paper as contained within a unit area flat planar projection of that tissue paper. Generally, this amount of surface area is greater than the surface area obtained by measuring the projected planar dimensions of the tissue paper. The user may desire a first surface area for shipment and storage, and a second surface area for use.

Likewise, the user may desire to have a tissue paper with multiple exposed edges which can provide for cleaning. The edges provide a scraping action for removal of the material to be cleaned. This can be particularly advantageous when the product is used as a bath tissue or other cleaning implement. It is believed that the greater surface area provided to the tissue paper of the present invention upon activation ultimately yields more usable area for cleaning. Particularly, each edge of the slit provides an opportunity for scraping foreign material from the surface to be cleaned. Foreign material can become entrapped in the voids between slits allowing for further efficacy in cleaning. This improved cleaning efficacy may manifest itself as an increase in the coefficient of friction of the tissue paper.

Likewise, if the tissue paper according to the present invention is to be used as a bath tissue, high void volume upon activation prophetically provides for improved flushability. One attempt in the art to make a toilet paper having improved flushability is found in U.S. Pat. No. 5,652,035, issued Jul. 29, 1997, to Tseng. This patent discloses a bath tissue paper divided into quadrants. Diagonally opposed quadrants have slits which are parallel. The tissue paper has two pairs of diagonally opposed quadrants. Each pair has slits which are mutually parallel to the slits in the diagonally opposed quadrant and mutually perpendicular to the slits in the adjacent quadrants. While this arrangement may provide improved flushability, it does not allow the consumer to readily activate the tissue paper by application of tensile forces. As the user grasps the tissue and pulls it apart, the slits which are perpendicular to the line of the tensile force will tend to open the tissue paper while the slits which are parallel to the application of the tensile force will generally not be extensible. The tissue will not properly activate as described below.

Commonly assigned U.S. Pat. No. 3,895,128, issued Jul. 15, 1975 to Gaisser, incorporated herein by reference, discloses a fabric conditioner article usable as a dryer-added fabric softener. Commonly assigned U.S. Pat. No. 3,944,694, issued Mar. 16, 1976 to McQueary, and U.S. Pat. No. 3,956,556, issued May 11, 1976 to McQueary, both incorporated herein by reference, disclose fabric conditioning articles having slits and perforations therein. These fabric conditioner articles are also usable as dryer-added fabric softeners. The purpose of the slits and perforations is to allow air flow through the fabric conditioning article, thereby preventing obstruction of the exhaust when used as a dryer-added fabric softener. If a substrate according to the present invention is to be used as a dryer-added fabric softener, activation of the substrate at the point of use provides a low density/high void volume substrate, particularly well suited for air flow therethrough during use in the dryer.

Another application of slitting technology is found in U.S. Pat. No. 5,667,871, issued Sep. 16, 1997, to Goodrich et al. Goodrich et al. uses an exemplary 70 pound natural Kraft paper to form filling material. The material is used to fill hollow spaces in packaging or the like. Likewise, U.S. Pat. No. 5,365,819, issued Nov. 22, 1994 to Maida et al., teaches a process for forming a packing material using a multitude of slits. The slits allow the material to be expanded into a three-dimensional shape that is both load-bearing and resilient.

Yet another example of the slitting technology is illustrated in U.S. Pat. No. 5,374,381, issued Dec. 20, 1994, to Schuld et al. Schuld et al. teaches an evaporative element or cartridge especially useful in humidifiers. The element comprises multiple layers of slit and expanded wicking material made of blotter-type paper. A metal layer or other frame is provided for structural strength.

A substrate according to the present invention may be used as a bath tissue, facial tissue, paper towel, napkin, rag, sponge, scrubby, poof, body wash, filter, face mask, pillow material, padding, insulation, packing material, bandage, wound dressing, dryer-added fabric softener, a core for absorbent products such as diapers, sanitary napkins or tampons, a drainage medium for outdoor use, bedding for plants, etc. The substrate, without regard to its end use, is activatable at the point of use or at an intermediate point in the manufacturing process.

SUMMARY OF THE INVENTION

The invention comprises a generally planar substrate of tissue paper. The tissue paper may comprise cellulosic and/or synthetic fibers. The tissue paper is provided with a pattern of lines of weakness. The lines of weakness may have a major axis. The lines of weakness may be disposed in a grid, may be of identical length and pitch or may comprise a variety of sizes and shapes. The major axes of the lines of weakness may be straight, parallel and/or oriented in a common direction. The lines of weakness may also be curvilinear and oriented in various diagonal relationships.

The tissue paper may be plastically activated in tension. The activation direction may be generally perpendicular to the major axies of the lines of weakness. Upon activation the tissue paper is transformed from a first state of intensive properties to a second state of intensive properties. For example, upon activation, the Z direction thickness of the tissue paper will increase.

BRIEF DESCRIPTION OF THE FIGURES

FIG. 13A also shows the response to activation of Quilted Northern Ultra bath tissue and Brawny paper towels, both made by the Fort James Corporation, and Kleenex facial tissue made by the Kimberly Clark Corporation.

DETAILED DESCRIPTION OF THE INVENTION

Figure 1:
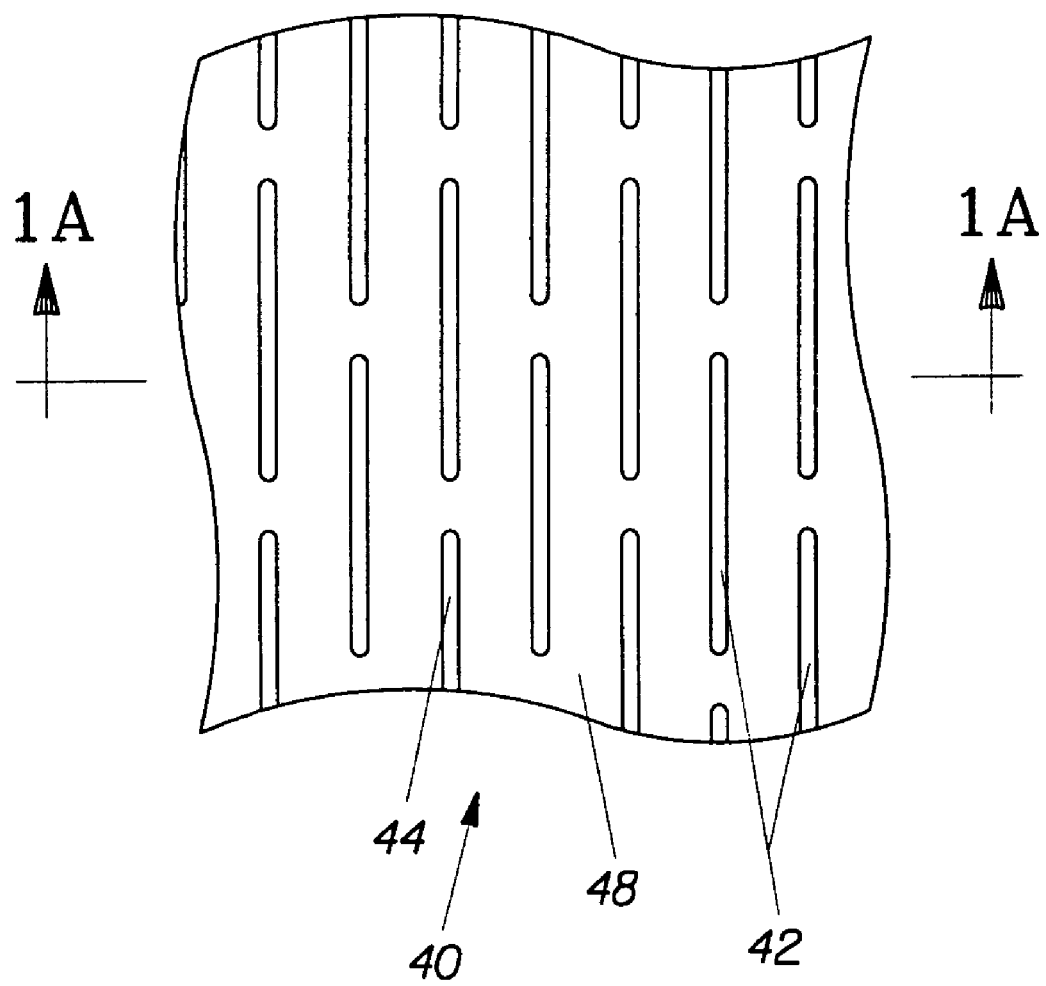
FIG. 1 is a fragmentary top plan view of an exemplary tissue paper according to the present invention prior to activation and having straight, parallel and unilaterally offset slits. The slits in FIG. 1 were made in papermaking as low basis weight regions.
Figure 2:
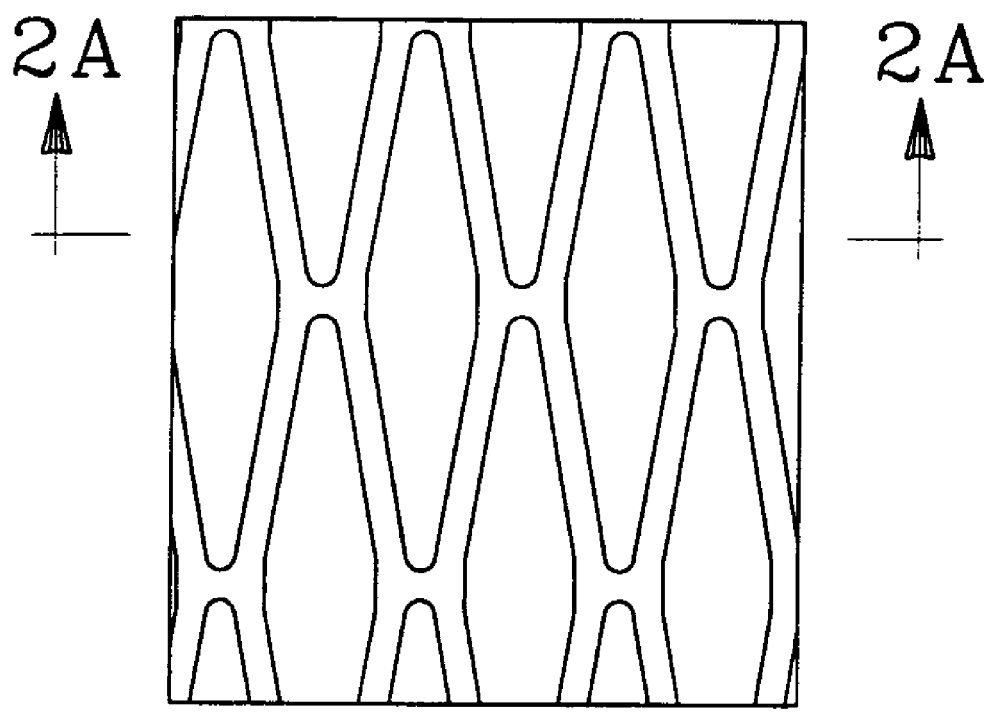
FIG. 2 is a fragmentary top plan view of the tissue paper of FIG. 1 following activation.
Figure 3:
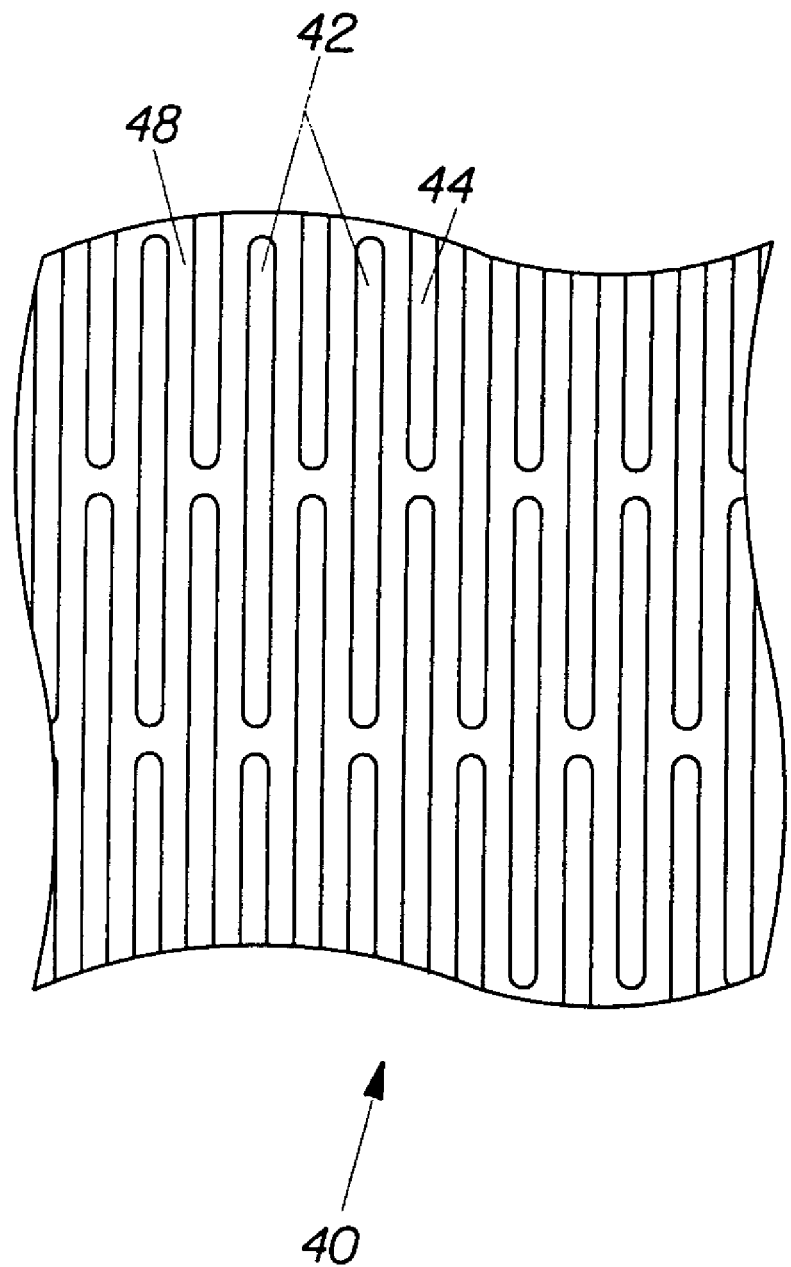
FIG. 3 is a fragmentary top plan view of an exemplary tissue paper according to the present invention prior to activation and having straight, parallel and unilaterally offset slits, the slits of the tissue paper of FIG. 3 having a discernible width. The slits in FIG. 3 were made during papermaking as low basis weight regions, but having a higher basis weight than the corresponding slits of FIG. 1.
Figure 4:
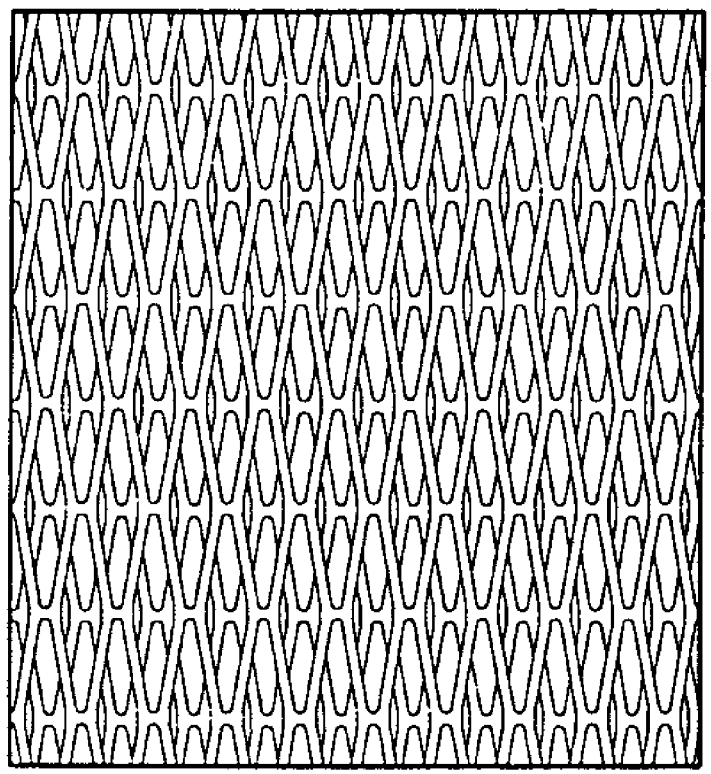
FIG. 4 is a fragmentary top plan view of the tissue paper of FIG. 3 following activation.
Figure 5:
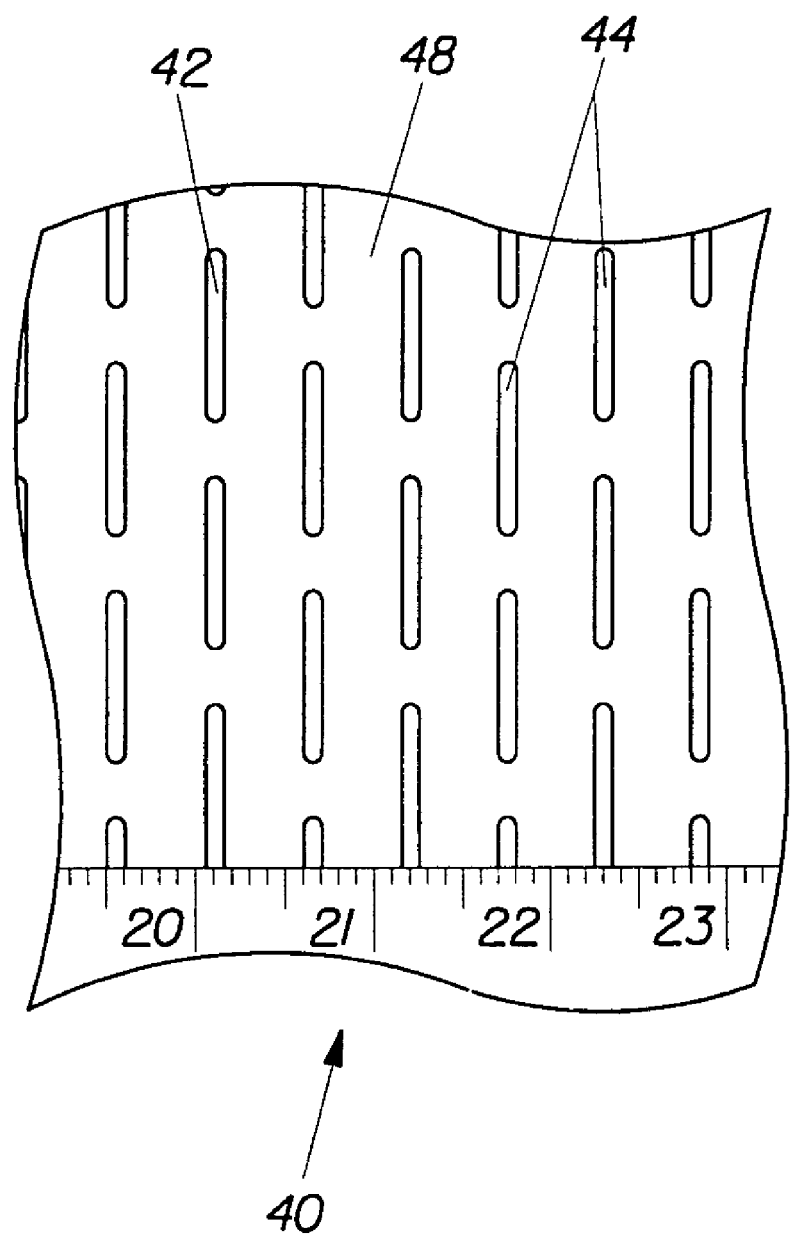
FIG. 5 is a fragmentary top plan view of an exemplary tissue paper according to the present invention prior to activation and having straight, parallel and unilaterally offset slits, the slits of the tissue paper of FIG. 5 having a discernible width. The slits in FIG. 5 were made during papermaking as low basis weight regions, and are of one-half the length of the slits in FIG. 3.
Figure 6:
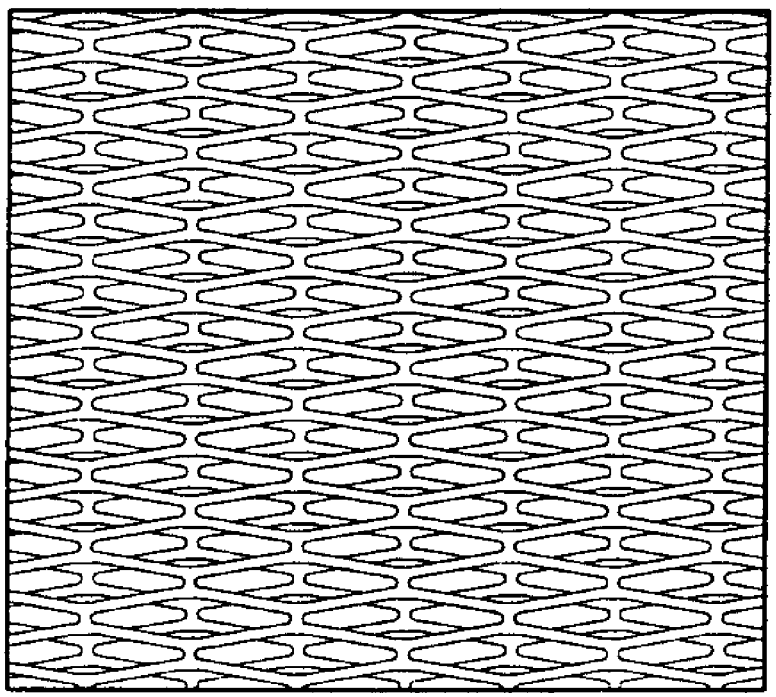
FIG. 6 is a fragmentary top plan view of the tissue paper of FIG. 5 following activation.
Figure 7:
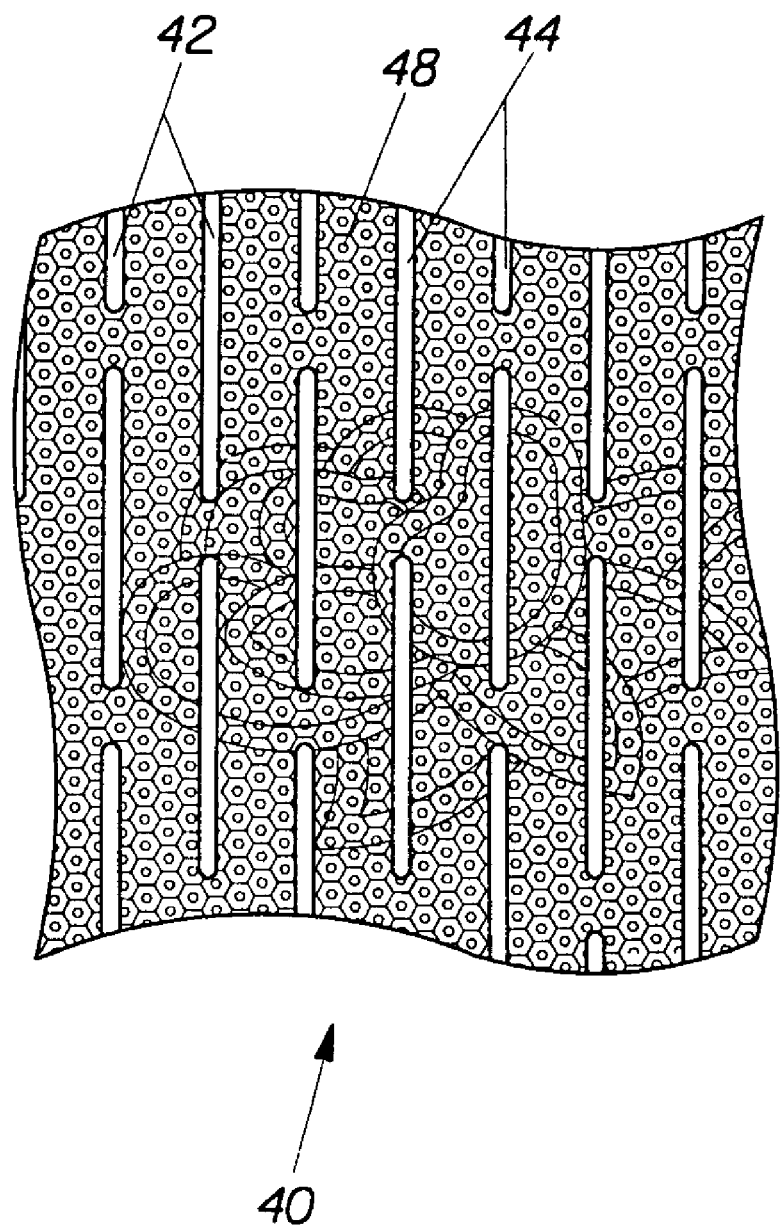
FIG. 7 is a fragmentary top plan view of an exemplary tissue paper according to the present invention prior to activation and having straight, parallel and unilaterally offset slits. The substrate for the tissue paper of FIG. 7 is Charmin Ultra-type bath tissue, with the forming wire side facing the viewer. The tissue paper of FIG. 7 was made using a rotary slitter.
Figure 8:
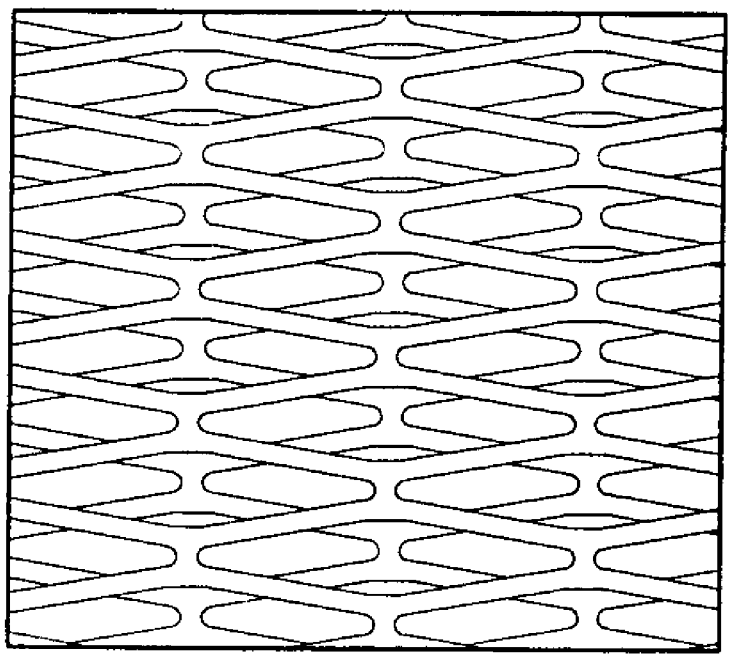
FIG. 8 is a fragmentary top plan view of the tissue paper of FIG. 7 following activation.

Referring to FIGS. 1–12, the present invention comprises a sheet of a flexible, macroscopically planar substrate. The substrate will be discussed below in a first execution as tissue paper 40, although it is to be understood alternative executions and materials are within the scope of the claimed invention. The sheet of tissue paper 40 has a machine direction and cross machine direction orthogonal thereto. Collectively, these two directions define an XY plane and a Z-direction orthogonal to the XY plane. The tissue paper 40 may be of indeterminate length. It is to be understood that while rectangular-shaped tissue papers 40 are illustrated, other shapes such as circles, regular and irregular polygons, etc., are within the scope of the present invention.

The tissue paper 40 comprises a plurality of lines of weakness 42 extending substantially or entirely through the thickness of the tissue paper 40 in the Z-direction. The lines of weakness 42 may be slits 44, cuts, perforations, apertures, areas of significantly reduced basis weight or any other artifact in the tissue paper 40 which allows it to form an essentially continuous network with holes dispersed throughout the network when activated as discussed below.

Activation of the tissue paper 40 refers to a plastic change in one or more intensive properties of the tissue paper 40. To activate the tissue paper 40, it is elongated in tension by the application of tensile forces. The applied tensile forces may be generally perpendicular to the major axis of the lines of weakness 42, so that maximum elongation occurs.

During activation, the tissue is plastically extended, by opposed tensile forces. The tensile forces occur in a direction having a vector component perpendicular to, and preferably which is identically perpendicular to, the major axis of the lines of weakness 42. By plastic extension, it is meant that the tissue paper 40 permanently increases in length or thickness in response to the application of opposed tensile forces. The increased length may relax somewhat after the applied tensile forces are removed, but the tissue paper 40 does not return to its original length.

The tissue paper 40 may be cellulosic, and conventionally dried or through air dried using known papermaking techniques. The tissue paper 40 may be of constant or variable basis weight and/or density, with a particularly preferred multi-basis weight embodiment being described below. The tissue paper 40 according to the present invention may be made according to any of commonly assigned U.S. Pat. No. 4,529,480, issued Jul. 16, 1985 to Trokhan; U.S. Pat. No. 4,637,859, issued Jan. 20, 1987 to Trokhan; U.S. Pat. No. 5,364,504, issued Nov. 15, 1994 to Smurkoski et al.; U.S. Pat. No. 5,529,664, issued Jun. 25, 1996 to Trokhan et al.; U.S. Pat. No. 5,679,222 issued Oct. 21, 1997 to Rasch et al.; U.S. Pat. No. 5,714,041 issued Feb. 3, 1998 to Ayers et al.; U.S. Pat. No. 5,906,710, issued May 25, 1999 to Trokhan; U.S. Pat. No. 5,980,691, issued Nov. 9, 1999 to Weisman et al., U.S. Pat. No. 5,549,790, issued Aug. 27, 1996 to Phan; U.S. Pat. No. 5,556,509, issued Sep. 17, 1996 to Trokhan et al.; U.S. Pat. No. 5,580,423, issued Dec. 3, 1996 to Ampulski et al.; U.S. Pat. No. 5,609,725, issued Mar. 11, 1997 to Phan; U.S. Pat. No. 5,629,052 issued May 13, 1997 to Trokhan et al.; U.S. Pat. No. 5,637,194, issued Jun. 10, 1997 to Ampulski et al.; U.S. Pat. No. 5,674,663, issued Oct. 7, 1997 to McFarland et al.; U.S. Pat. No. 5,693,187 issued Dec. 2, 1997 to Ampulski et al.; U.S. Pat. No. 5,709,775 issued Jan. 20, 1998 to Trokhan et al.; U.S. Pat. No. 5,776,307 issued Jul. 7, 1998 to Ampulski et al.; U.S. Pat. No. 5,795,440 issued Aug. 18, 1998 to Ampulski et al.; U.S. Pat. No. 5,814,190 issued Sep. 29, 1998 to Phan; U.S. Pat. No. 5,817,377 issued Oct. 6, 1998 to Trokhan et al.; U.S. Pat. No. 5,846,379 issued Dec. 8, 1998 to Ampulski et al.; U.S. Pat. No. 5,855,739 issued Jan. 5, 1999 to Ampulski et al.; U.S. Pat. No. 5,861,082 issued Jan. 19, 1999 to Ampulski et al., U.S. Pat. No. 5,871,887 issued Feb. 16, 1999 to Trokhan et al.; U.S. Pat. No. 5,897,745 issued Apr. 27, 1999 to Ampulski, et al.; U.S. Pat. No. 5,904,811 issued May 18, 1999 to Ampulski et al.; and U.S. Pat. No. 6,051,105, issued Apr. 18, 2000 to Ampulski, the disclosures of which are incorporated herein by reference.

Alternatively, the tissue may be made without creping. Tissue made without creping is illustrated by U.S. Pat. No. 5,392,068, issued Aug. 3, 1999 to Farrington, Jr. et al.

If the tissue paper 40 selected for use with the present invention comprises multiple densities, or multiple basis weights as discussed below, and is through air dried, one of skill may wish to utilize micropore drying to remove water from the tissue paper 40 during manufacture. In micropore drying a flow restriction is placed in the path of the through drying air flow. The micropore medium has pores smaller than the interstices of the tissue paper 40 to be dried. Micropore drying may be conducted in accordance with the following commonly assigned patents, incorporated herein by reference: U.S. Pat. No. 5,274,930, issued Jan. 4, 1994 to Ensign et al.; U.S. Pat. No. 5,437,107, issued Aug. 1, 1995 to Ensign et al.; U.S. Pat. No. 5,539,996, issued Jul. 30, 1996 to Ensign et al.; U.S. Pat. No. 5,581,906, issued Dec. 10, 1996 to Ensign et al.; U.S. Pat. No. 5,584,126, issued Dec. 17, 1996 to Ensign et al.; U.S. Pat. No. 5,584,128, issued Dec. 17, 1996 to Ensign et al.; U.S. Pat. No. 5,625,961, issued May 6, 1997 to Ensign et al.; U.S. Pat. No. 5,912,072, issued Jun. 15, 1999 to Trokhan et al.; U.S. Pat. No. 5,942,322, issued Aug. 24, 1999 to Ensign et al.; U.S. Pat. No. 6,021,583, issued Feb. 8, 2000 to Stelijes et al; and U.S. Pat. No. 6,105,276, issued Aug. 22, 2000 to Ensign et al.

Alternatively, as noted above, substrates which are non-cellulosic in whole or in part are included within the scope of the present invention. The substrate according to the present invention may comprise cellulosic fibers, synthetic fibers and mixtures thereof. One suitable apparatus for producing a non-woven fabric according to the present invention is illustrated in commonly assigned U.S. Pat. No. 5,895,623, issued Apr. 20, 1999 to Trokhan et al., and incorporated herein by reference.

Examining the tissue according to the present invention in more detail, the tissue has a plurality of lines of weakness 42. The lines of weakness 42 will be discussed hereinbelow as slits 44, although it is to be recognized the invention is not so limited. The lines of weakness 42 may comprise perforations, apertures, etc. As used herein, a perforation comprises a discontinuity or interruption in the tissue which does not go all the way through the Z-direction thickness of the tissue and is essentially unidimensional within the XY plane. A perforation may be made by cutting or by permanently compressing/deforming the fibers in the tissue. A slit will have a discernible first direction and be essentially linear with little discernible dimension in the perpendicular direction. A slit extends entirely throughout the Z-direction thickness of the tissue paper 40. Slits 44 and apertures may be essentially rectilinear or curvilinear. In contrast, an aperture is another type of line of weakness. The aperture has a discernible dimension in both the X and Y directions. Apertures may be thought of as holes which extend partially throughout the thickness of the tissue paper 40 or entirely throughout the thickness of the paper. Thus, both blind holes and through holes are included as apertures. The perforations, slits 44, apertures or other lines of weakness 42, may form a grid. Between the lines of weakness 42 are lands 48. The lands 48 become the mesh that defines the volume of the tissue upon activation.

For purposes of this discussion, the slits 44 are considered to be oriented in the machine direction, although it is to be recognized the slits 44 may be oriented in the cross machine direction, or at a diagonal relationship relative to the machine and cross machine directions. Alternatively, the tissue paper 40 may have slits 44 in both the machine and cross machine directions. The slits 44 may be unilaterally offset from one another. When the slits 44 are unilaterally offset, the end of one slit does not intercept the end of an adjacent slit which lies perpendicular to the major axis of the slits 44. Alternatively, the slits 44 may be bilaterally offset from adjacent slits 44, or may be aligned with adjacent slits 44.

Figure 27:
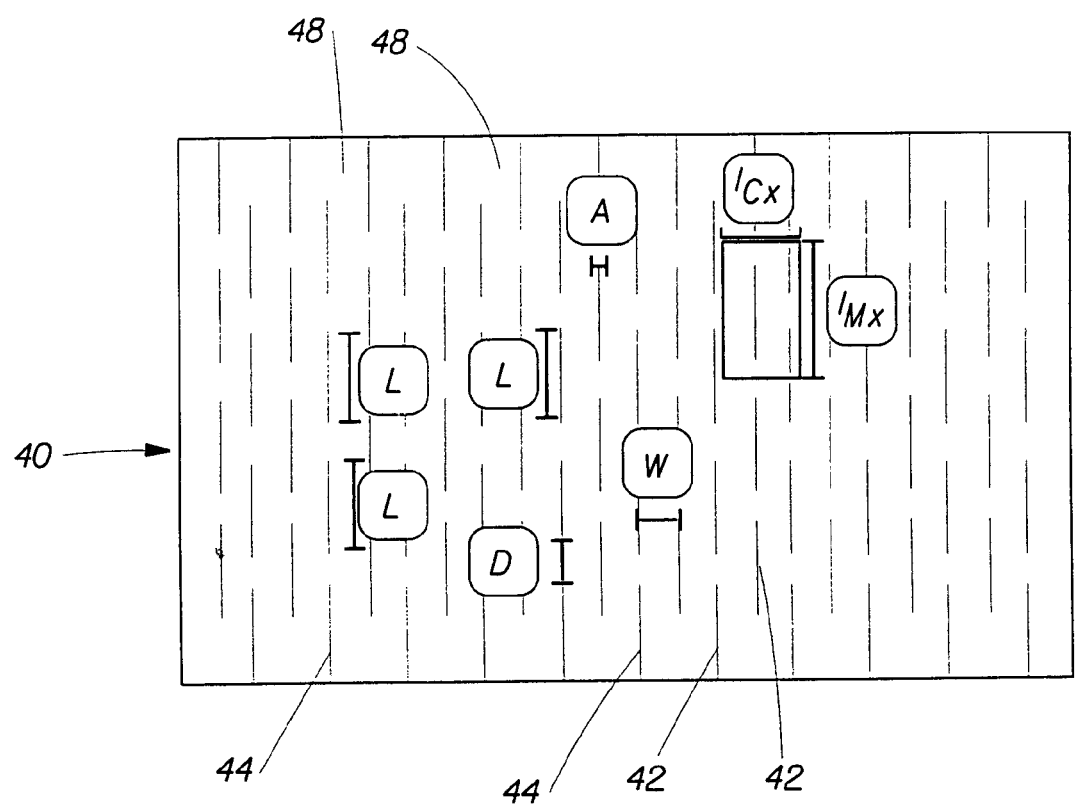
FIG. 27 is a schematic top plan view of an exemplary slit pattern, showing the dimensions used for analysis.

Referring to FIG. 27, the following notations are used to describe the invention pattern:

L is the length of the slits 44.

A is the width of the slits 44 prior to activation. The width of the slit is taken to approach zero, or to be zero, for a slit of infinitesimal width.

D is the distance between adjacent slits 44 in the length direction.

W is the distance between adjacent slits 44 in the width direction, i.e., the width of the lands 48. Generally, the slit length L will be greater than the distance between slits D so that greater elongation occurs upon activation in tension.

A unit cell is taken to be the smallest repeating unit which can be tesilated together to form the XY pattern of lands 48 and lines of weakness 42.

lmx is taken to be the length of the unit cell in the length direction of the slits 44 and is mathematically equivalent to the sum of L+D.

lcx is the length of the unit cell in the width direction and is mathematically taken to be the sum of 2W+2A.

Nm is the number of unit cells of the sheet taken in the length direction.

Nc is the number of unit cells of the sheet taken in the width direction.

The length L of the slit controls the size of the opening upon activation. Thus, the length L of the slit will impact the total elongation in the width direction. The distance between adjacent slits W defines the width of the lands 48 and controls the amount of expansion in the Z-direction and the general appearance of the tissue paper 40 when activated. The slit width A may be generally taken to be zero prior to activation. This width may have some contribution to the Z-direction expansion and provide for a particular type of mesh. For example, it may be desirable that the slits 44 provide a scooping action to remove foreign matter, dirt, etc. The distance between slits D controls the tensile strength in the width direction. The distance between slits W controls the Z-direction expansion, the tensile strength in the length direction, and will influence the size of any scoops or lands 48 upon activation. Such lands 48 will be oriented approximately 45 degrees to the plane of the substrate upon activation.

The following ratios influence the operation and properties of the tissue according to the present invention upon activation. L/W is the ratio of the length of the slit to the distance between adjacent slits 44, which distance is taken perpendicular to the major axis of the slits 44. The L/W ratio controls the amount of opacity, or the see-through area of the sheet upon activation. A lower L/W ratio results in greater opacity upon activation, while a higher L/W ratio will result in more open area and hence lower opacity upon activation.

L/D is the ratio of the slit length to the distance between adjacent slits 44 in the direction parallel to the slits 44. The L/D ratio is one factor which controls the amount of elongation perpendicular to the major axis of the slits 44 before structural failure occurs. A lower L/D ratio results in less elongation perpendicular to the slits 44 before structural failure, while a higher L/D ratio results in more elongation being achievable.

If the width of the lands W becomes too small, the tissue paper 40 will not have sufficient strength during activation and may rip into pieces upon activation. Alternatively, if the width of the lands W is too great, activation may require undue tensile force. Similarly, if the distance D between adjacent slits 44 is too small, the tissue paper 40 may rip upon activation.

A/W is the ratio of the width of the slit to the distance between adjacent slits 44, which distance is taken perpendicular to the major axis of the slits 44. The A/W is one factor which controls the amount of open area of the tissue prior to activation. A lower A/W ratio results in the less sheet open area, and hence greater opacity, before activation, while a higher A/W ratio results in more open area before activation.

While the slits 44 have a length L oriented in a first direction, it is to be recognized the tissue paper 40 is typically activated in a direction perpendicular to the length L, or major axis, of the slits 44. Thus, the length L of the tissue paper 40 is generally taken to be perpendicular to the length L of the slits 44. The width direction of the slit 44 or tissue paper 40 is perpendicular to the length direction of the slit 44.

Table 1 below illustrates known operating ranges for the parameters described above, for the embodiments of FIGS. 1–8. The numbers of different unit cells taken in the first and second directions are directly proportional to the complexity of the pattern of the tissue paper 40. In a degenerate case, an elaborate pattern may have one unit cell throughout the entire sheet.

TABLE 1

| Parameter | Lower Limit First Execution | Lower Limit Second Execution | Lower Limit Third Execution | Upper Limit First Execution | Upper Limit Second Execution | Upper Limit Third Execution |
|---|---|---|---|---|---|---|
| L/W | 0.1 | 1 | 2 | 100 | 10 | 5 |
| L/D | 0.1 | 1 | 2 | 100 | 20 | 10 |
| A/W | — | — | — | 10 | 2 | 1 |

Referring to FIGS. 9–12, alternative embodiments of tissue paper 40 according to the present invention are illustrated. This embodiment illustrates lines of weakness 42 oriented at a diagonal relative to the machine direction and cross machine direction. This arrangement provides the benefit that the tissue may be activated by opposed tensile forces oriented in either the machine direction, the cross-machine direction, or an angular relationship thereto. This arrangement also provides the benefit that for a multi-ply tissue, significant ply interaction occurs. It is believed that upon activation, the interlocking peaks of one ply will catch and maintain the loft, or the Z-direction expansion by interaction with adjacent plies in the multi-ply laminate.

Figure 9:
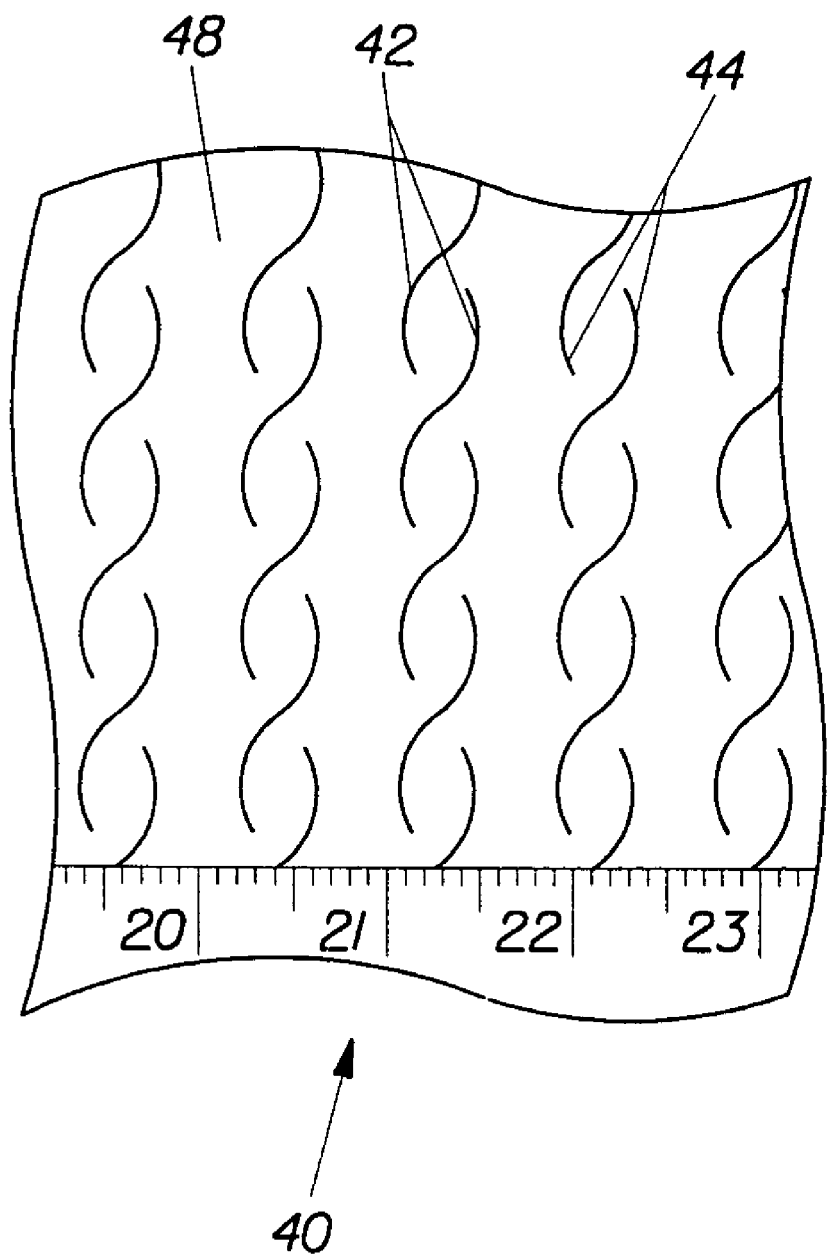
FIG. 9 is a fragmentary top plan view of the tissue paper having slits which form a broken sinusoidal pattern. The substrate of the tissue paper of FIG. 9 is Charmin-type bath tissue, with the forming wire side facing the viewer. The tissue paper of FIG. 9 was made using a laser cutter.
Figure 10:
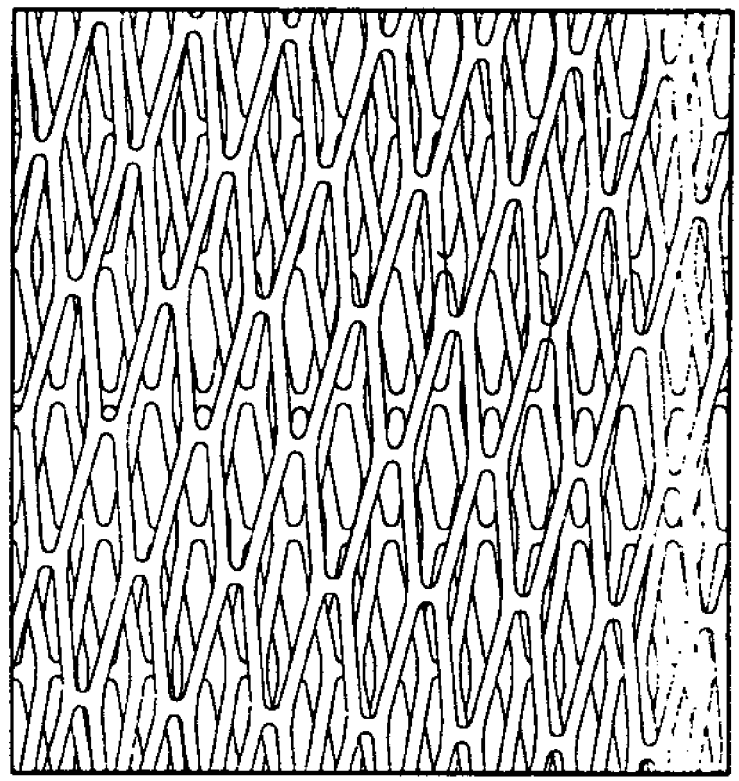
FIG. 10 is a fragmentary top plan view of the tissue paper of FIG. 9 following activation.
Figure 11:
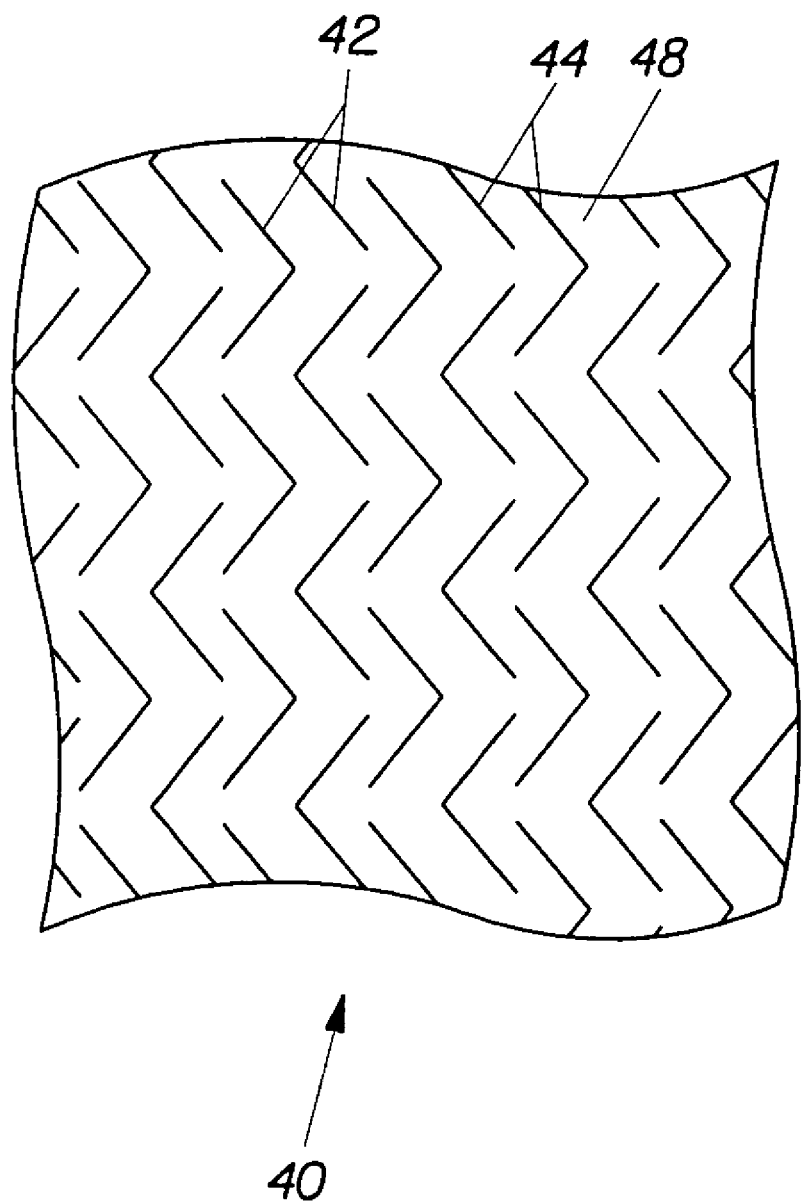
FIG. 11 is a fragmentary top plan view of the tissue paper according to the present invention having slits arranged in a interlaced bilaterally alternating chevron pattern. The tissue paper substrate of FIG. 11 is made of Charmin-type bath tissue, with the forming wire side oriented away from the viewer. The tissue paper of FIG. 11 was made using a laser cutter.
Figure 12:
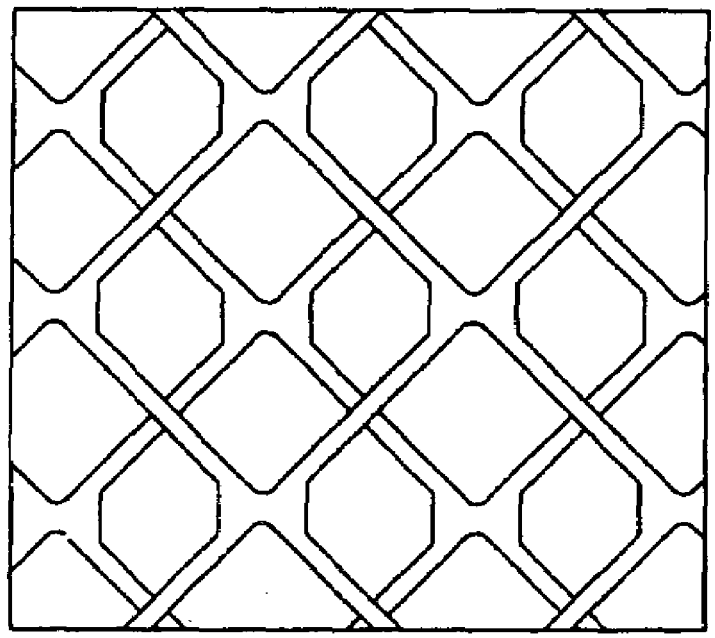
FIG. 12 is a fragmentary top plan view of the tissue paper of FIG. 11 following activation.
Figure 13A:
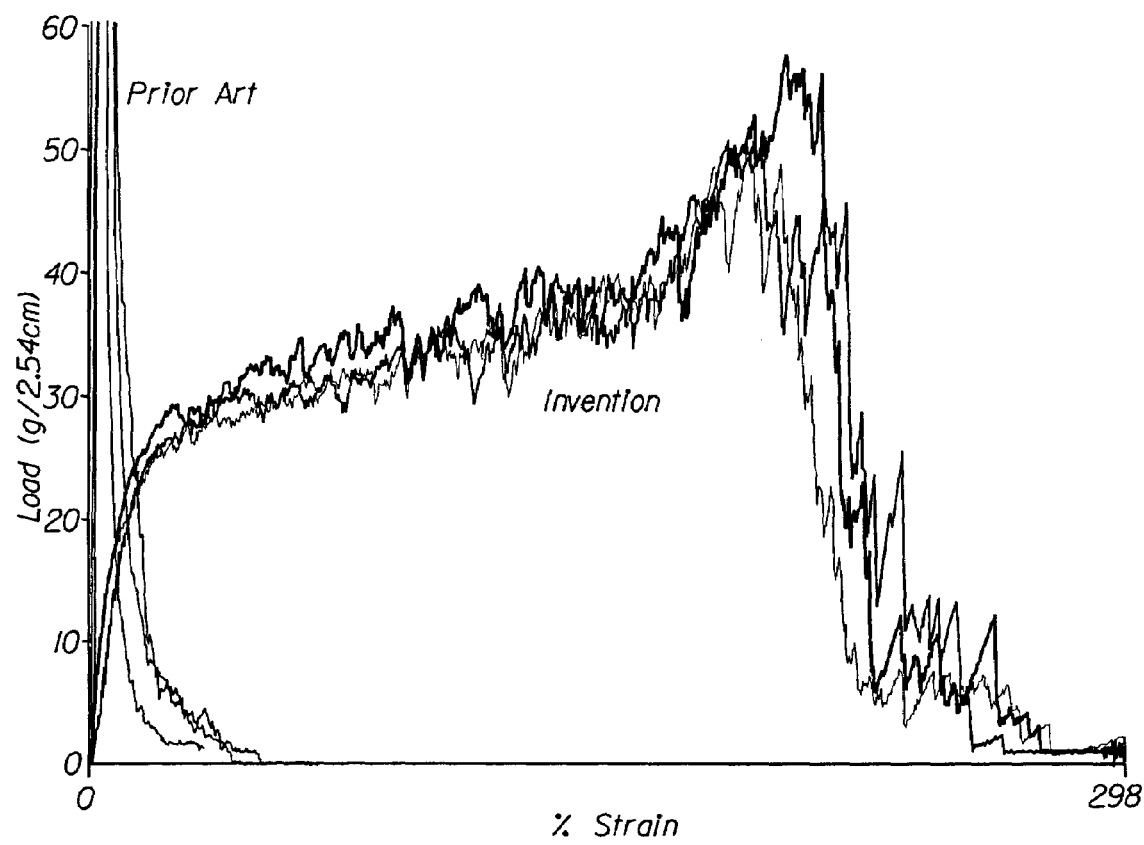
FIG. 13A is a load elongation curve showing the response to activation of the paper of FIGS. 1–2.
Figure 13B:
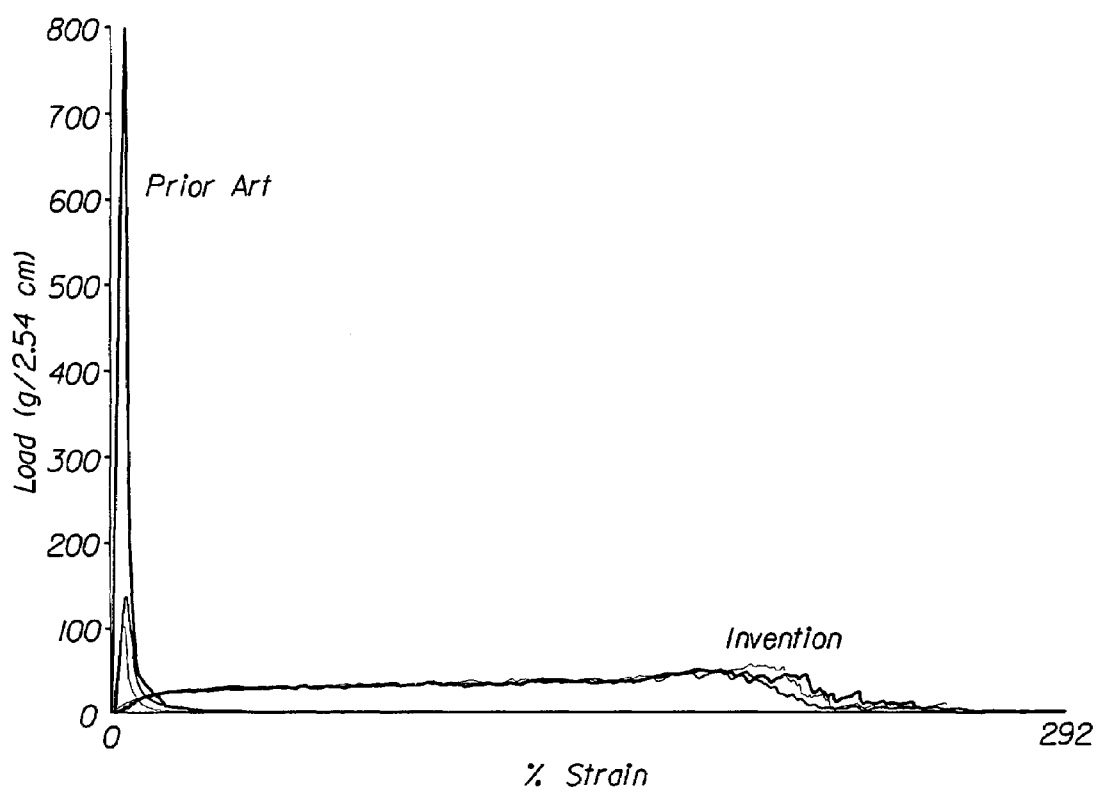
FIG. 13B is the load elongation curve of FIG. 13A, having a compressed strain scale.
Figure 14:
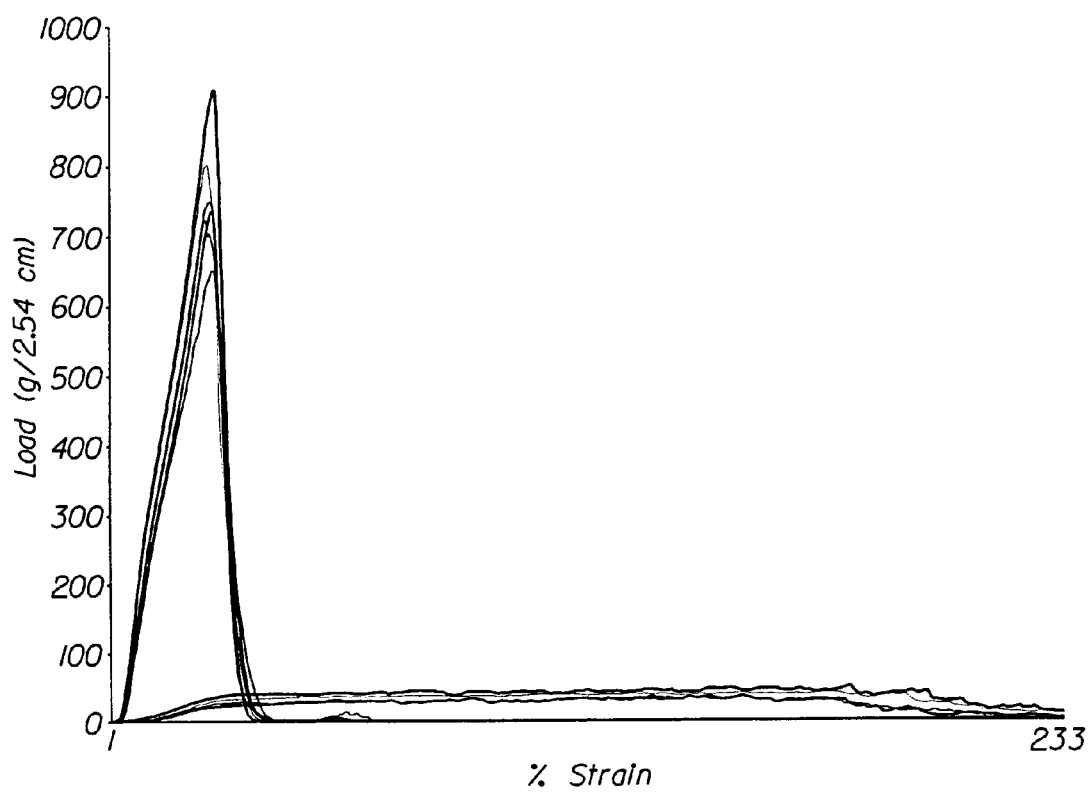
FIG. 14 is load elongations showing the response to activation of the paper of FIGS. 3–4.
Figure 15:
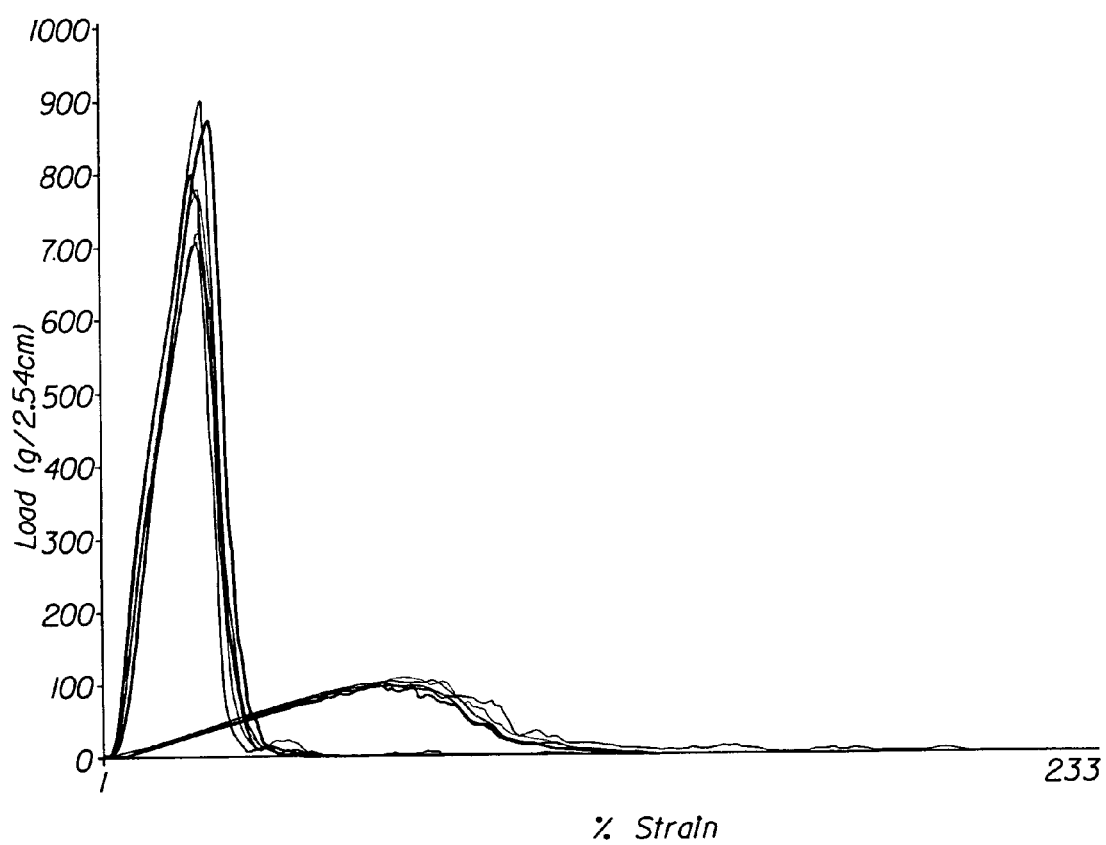
FIG. 15 is load elongations showing the response to activation of the paper of FIGS. 5–6.
Figure 16:
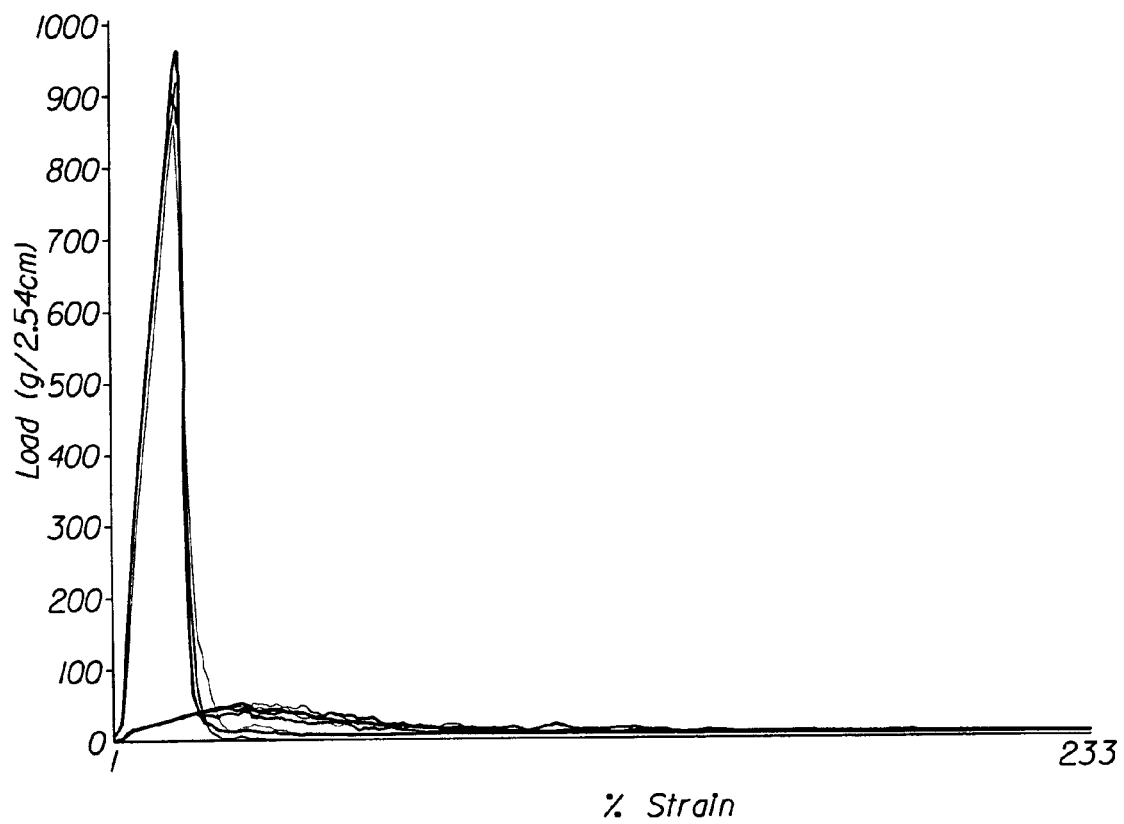
FIG. 16 is load elongations showing the response to activation of the paper of FIGS. 7–8.
Figure 17:
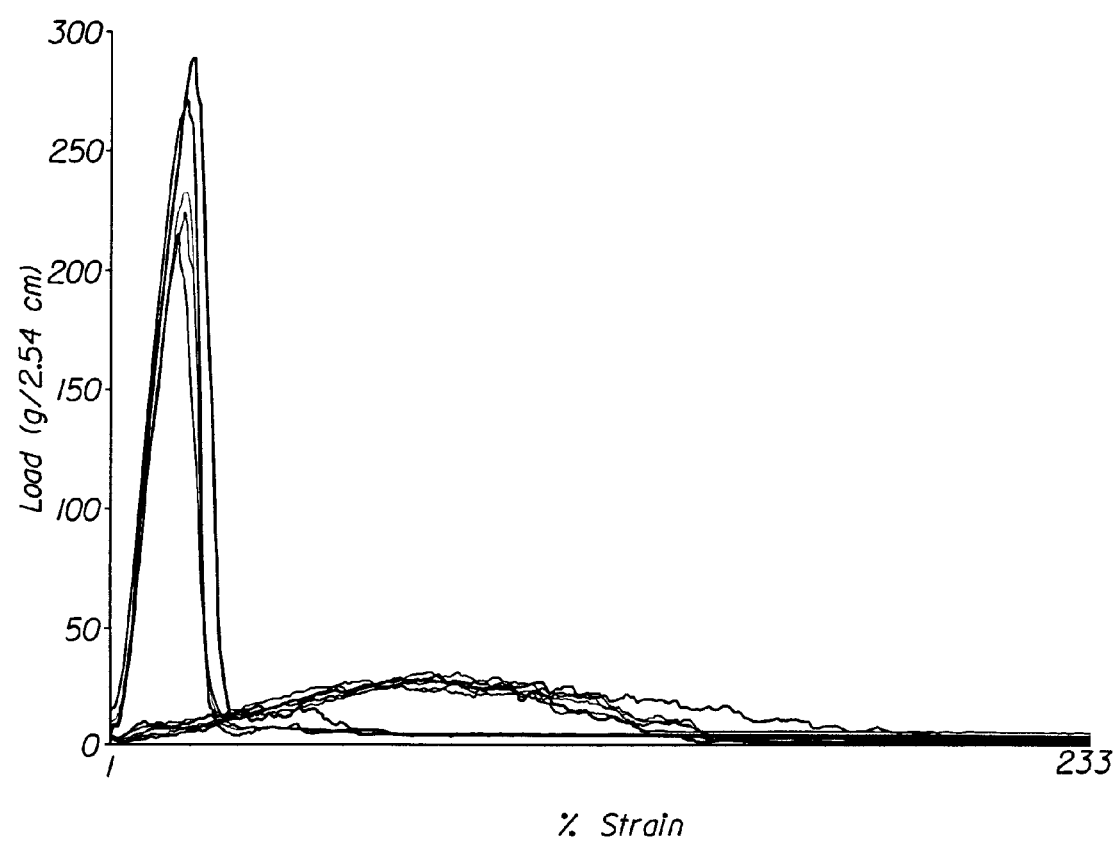
FIG. 17 is load elongations showing the response to activation of the paper of FIGS. 9–10.
Figure 18:
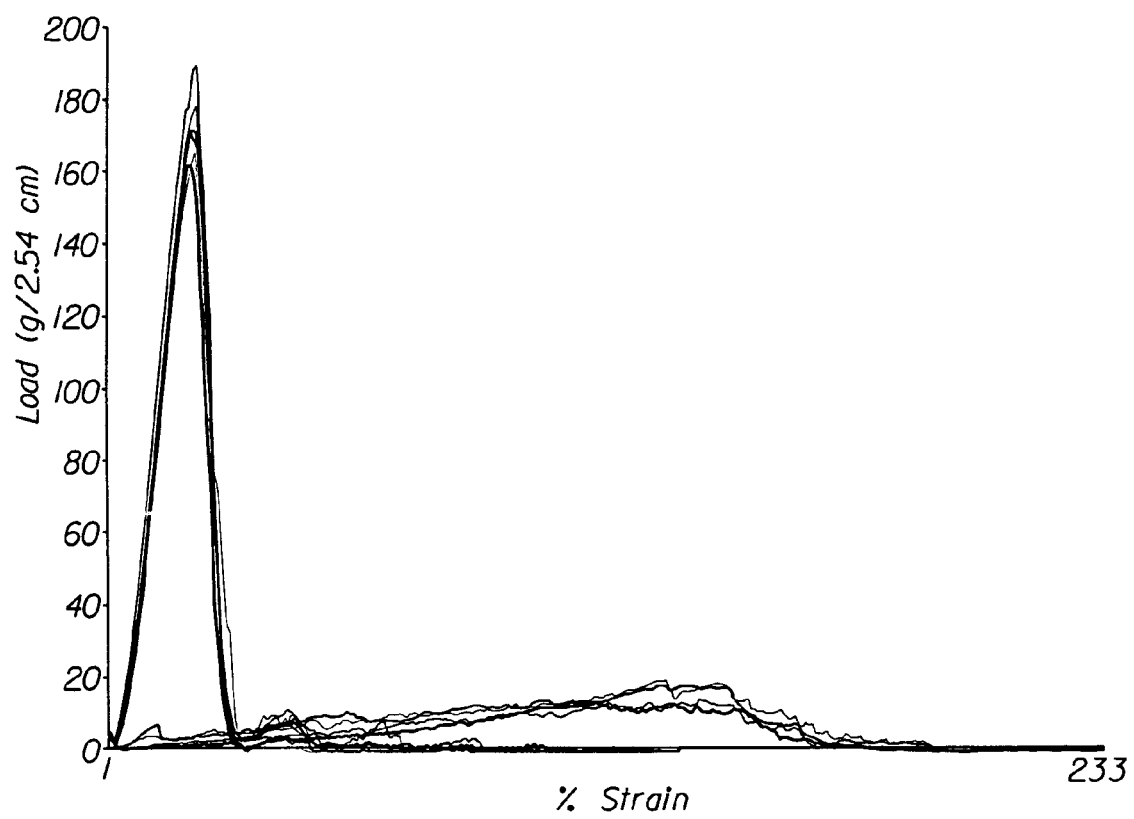
FIG. 18 is load elongation showing the response to activation of the paper of FIGS. 11–12.
Figure 19:
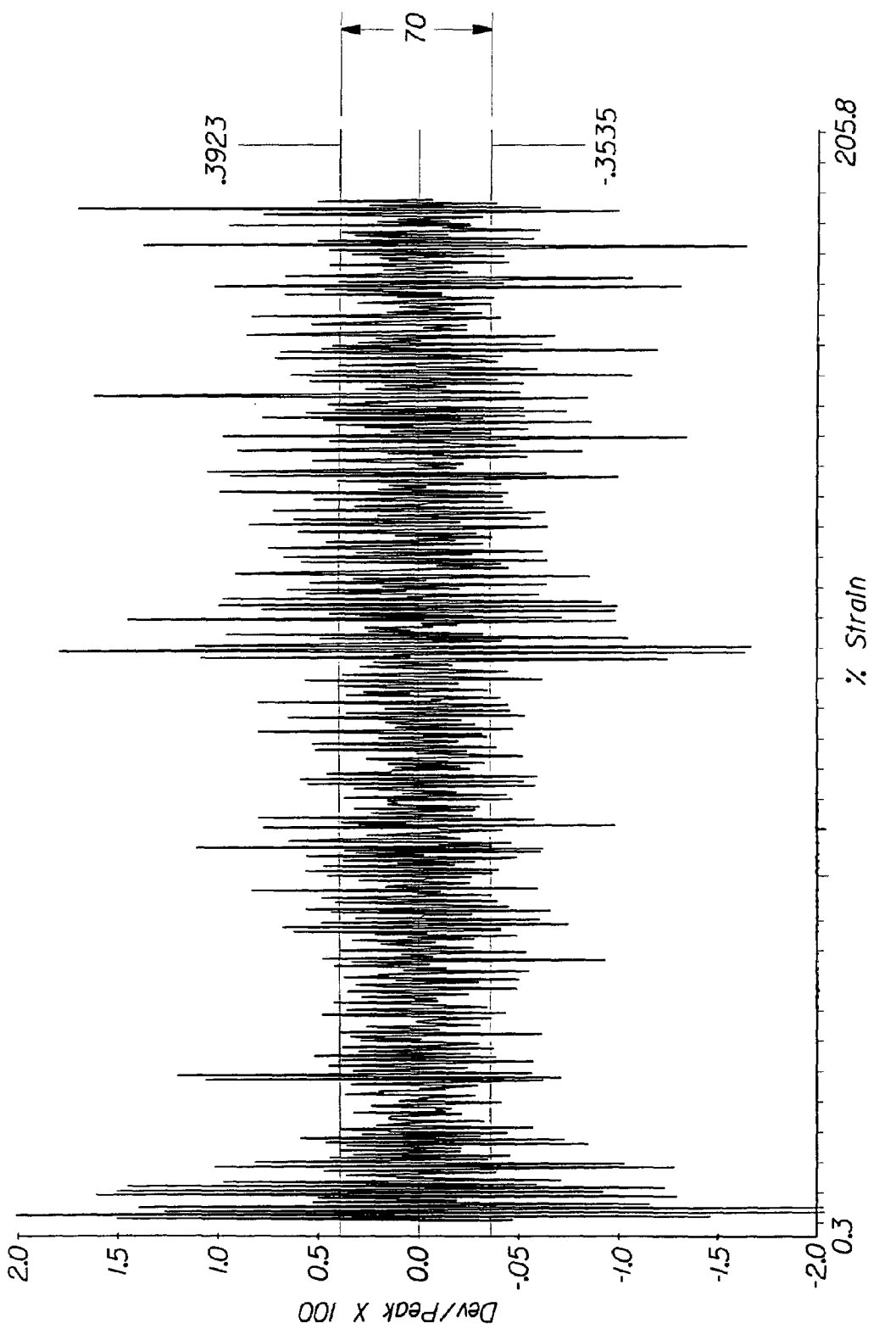
FIG. 19 is a graph of the bandwidth of the load elongation shown in FIGS. 13A–13B.
Figure 20:
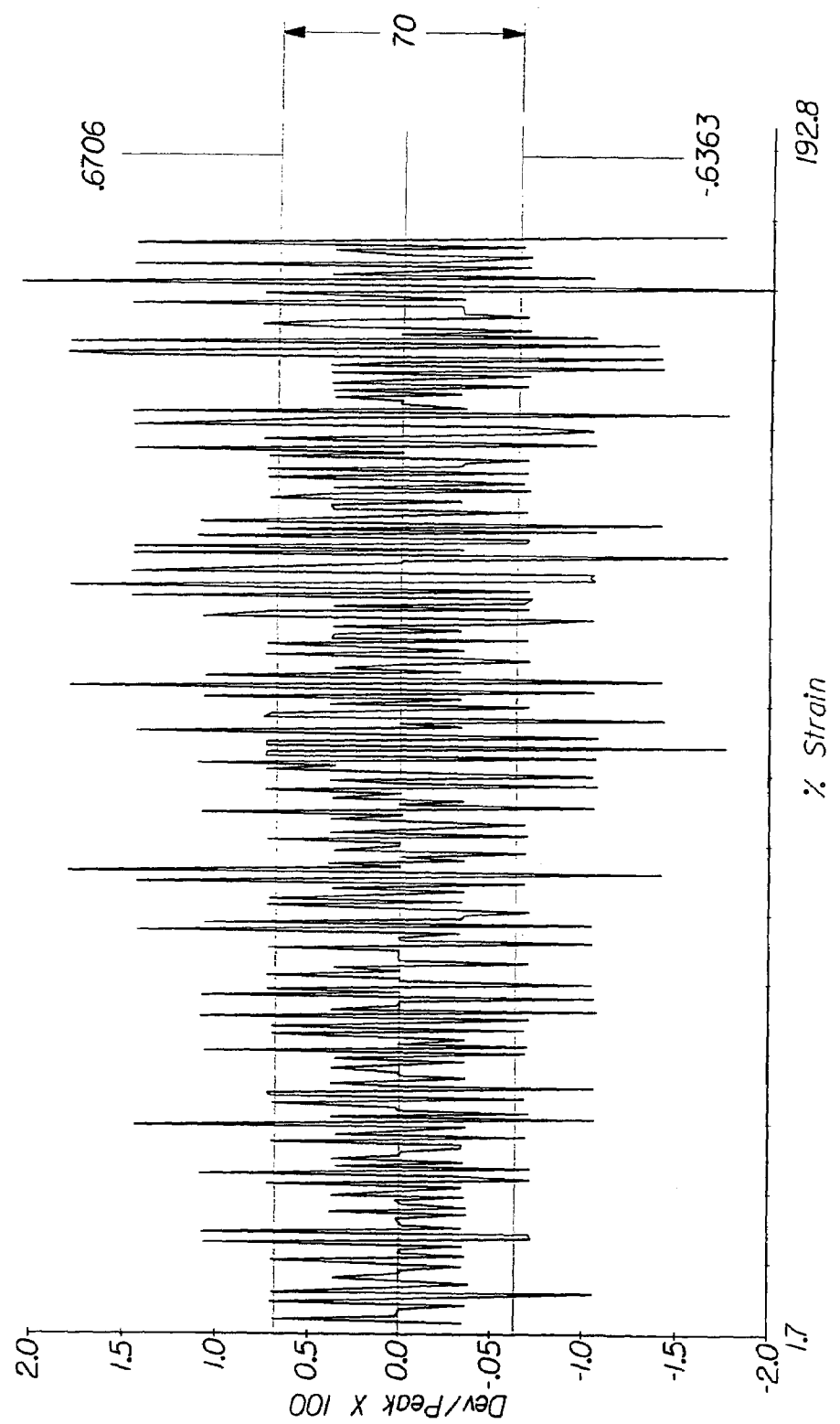
FIG. 20 is a graph of the bandwidth of the load elongation shown in FIG. 14.
Figure 21:
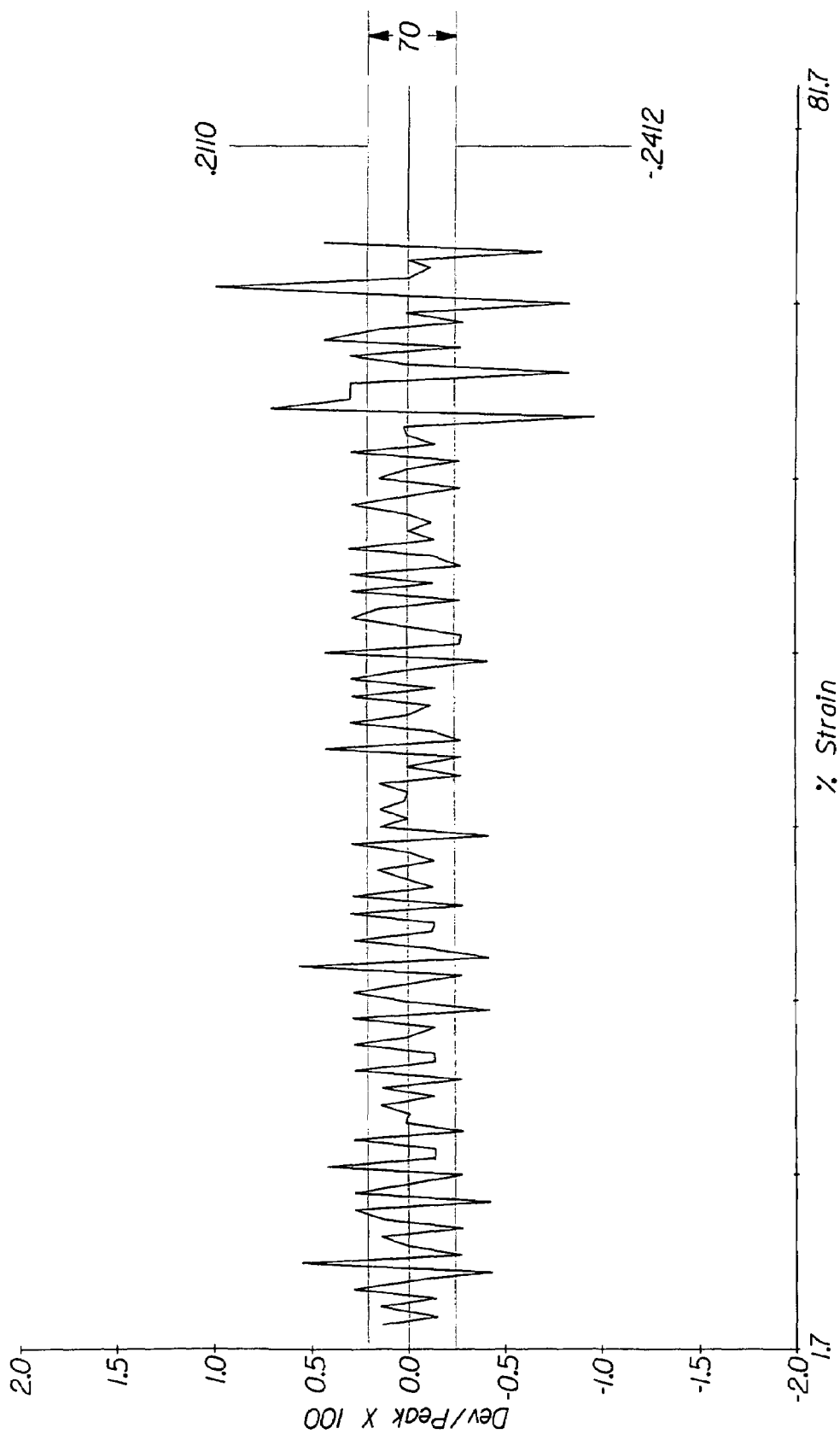
FIG. 21 is a graph of the bandwidth of the load elongation shown in FIG. 15.
Figure 22:
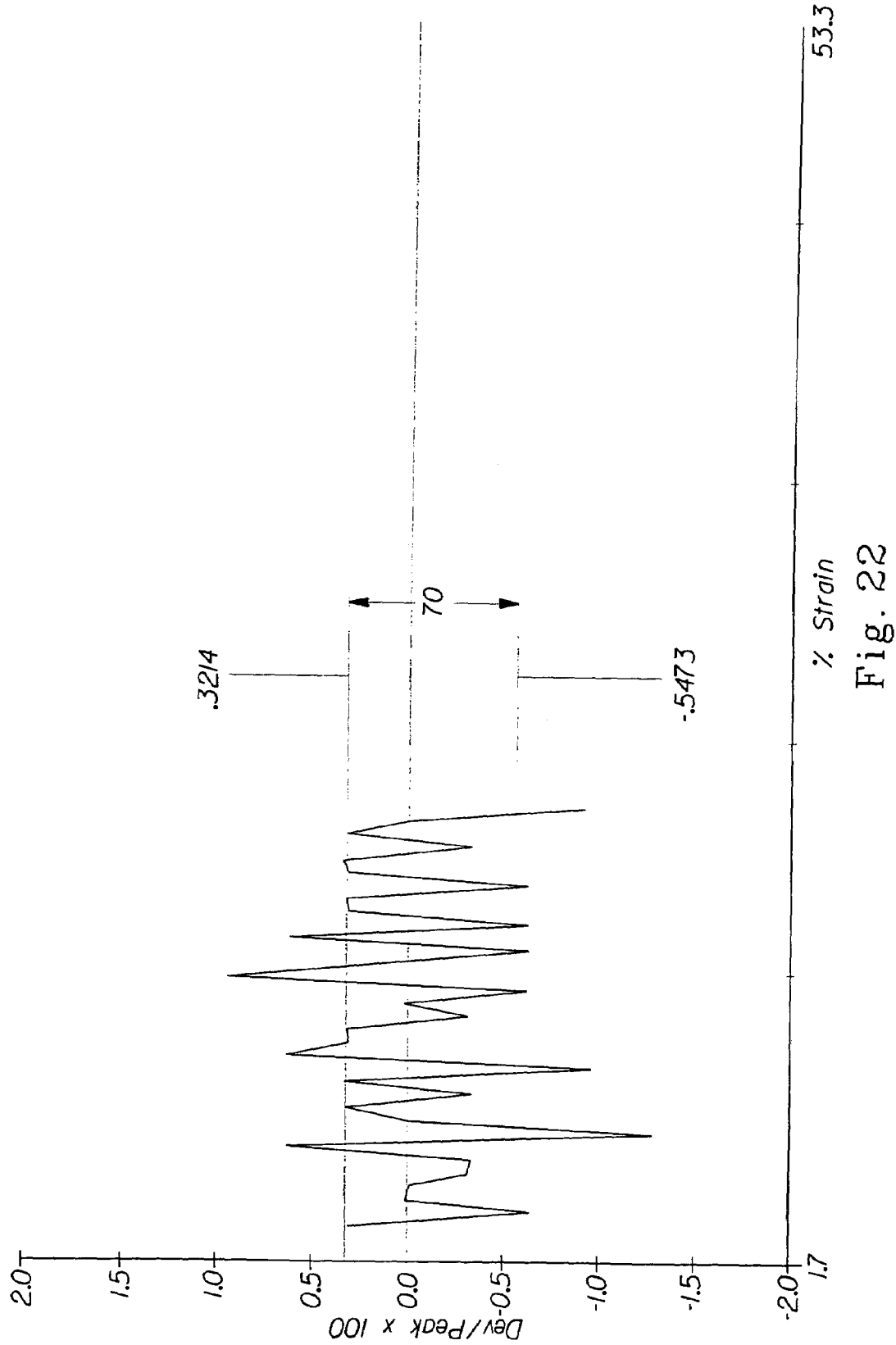
FIG. 22 is a graph of the bandwidth of the load elongation shown in FIG. 16.
Figure 23:
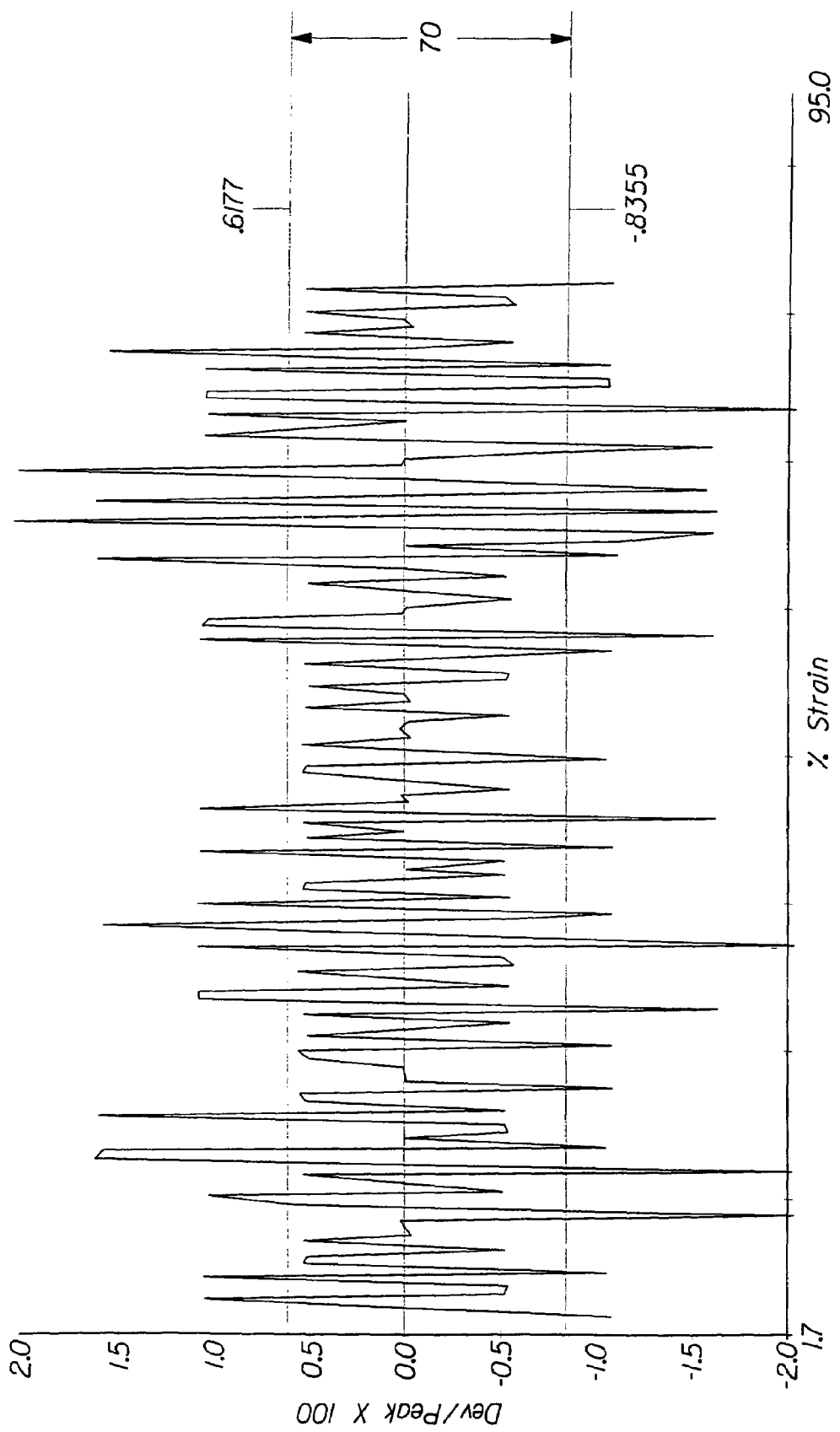
FIG. 23 is a graph of the bandwidth of the load elongation shown in FIG. 17.
Figure 24:
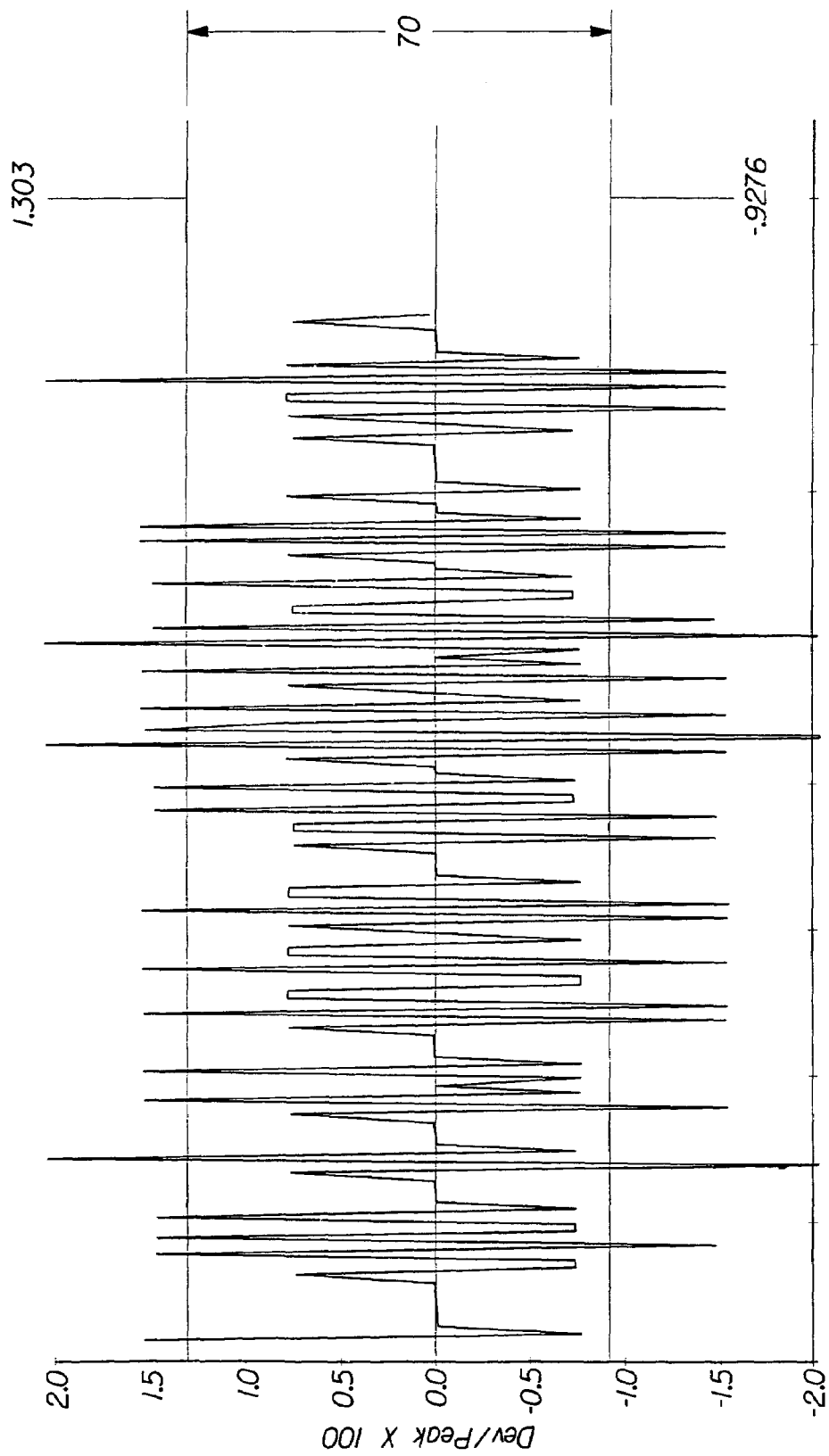
FIG. 24 is a graph of the bandwidth of the load elongation shown in FIG. 18.
Figure 25:
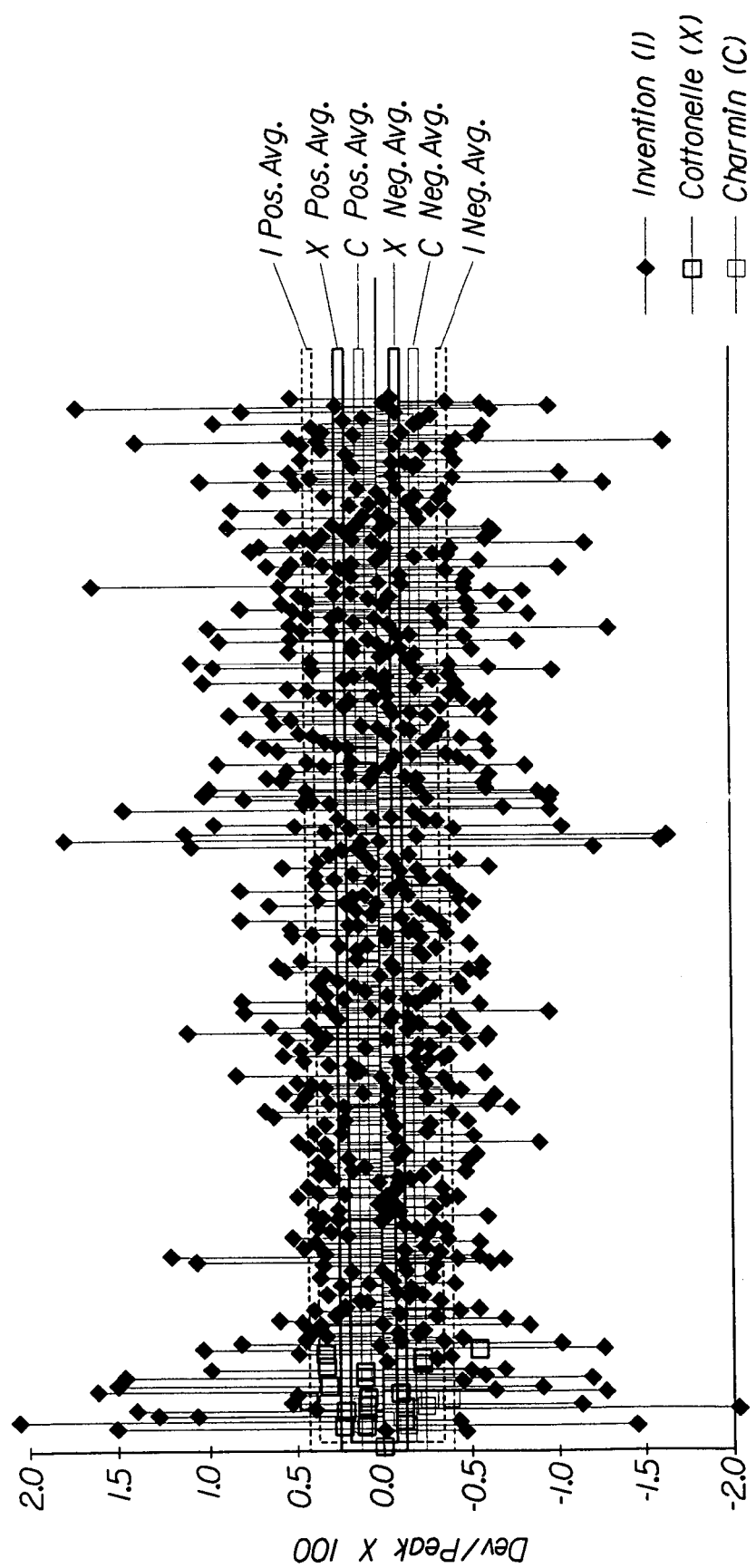
FIG. 25 is a graph of the bandwidth of the invention of FIG. 19 and prior art samples.

FIGS. 9–10 illustrate a tissue paper 40 having lines of weakness 42 which are sinusoidal and interlaced. If sinusoidal slits 44 are selected, adjacent slits 44 may be in phase, 180° out of phase, or at an intermediate phase. Alternatively, the slits 44 may be curvilinear and represent portions of circles, ovals, etc. If curvilinear slits 44 are selected, the slits 44 may be oriented with the concavity in the same direction, oriented with alternating slits 44 having opposed concavities, or an intermediate orientation. This arrangement also provides the benefit of being activatable by opposed tensile forces in either the machine direction, cross machine direction, or angular relationship thereto. The sinusoidal pattern provides rounded curves at the edges of the lands 48 upon activation. This arrangement provides the benefit there will be no rough points to abrade the consumer during use. Alternatively, as illustrated in FIGS. 11–12, the slits 44 need not be parallel. Alternating slits 44 may be oriented at diagonals relative to adjacent slits 44 and/or the machine and/or the cross machine directions. FIGS. 11–12 illustrate a tissue paper 40 pattern having chevron-shaped lines of weakness 42. It will be obvious to one of ordinary skill that a pattern of herringbone-shaped lines of weakness 42 may also be used.

Figure 29A:
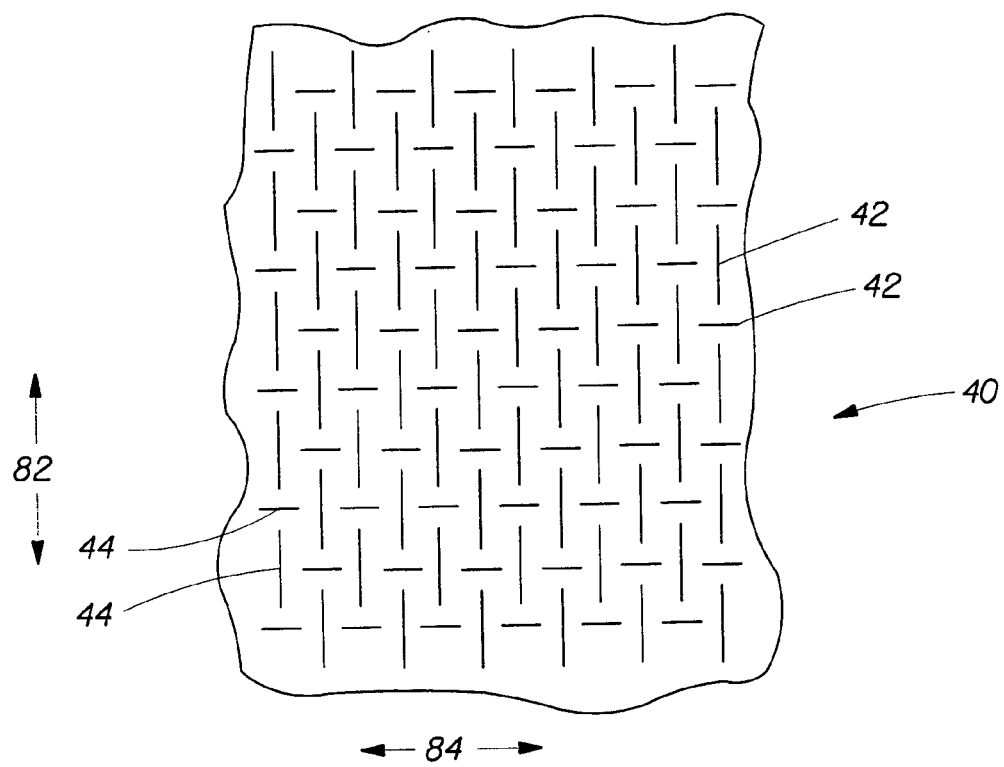
FIG. 29A is a fragmentary top plan view of a tissue paper having slits perpendicularly oriented in first and second directions wherein the slits in the first direction have a greater length than the slits in the second direction.
Figure 29B:
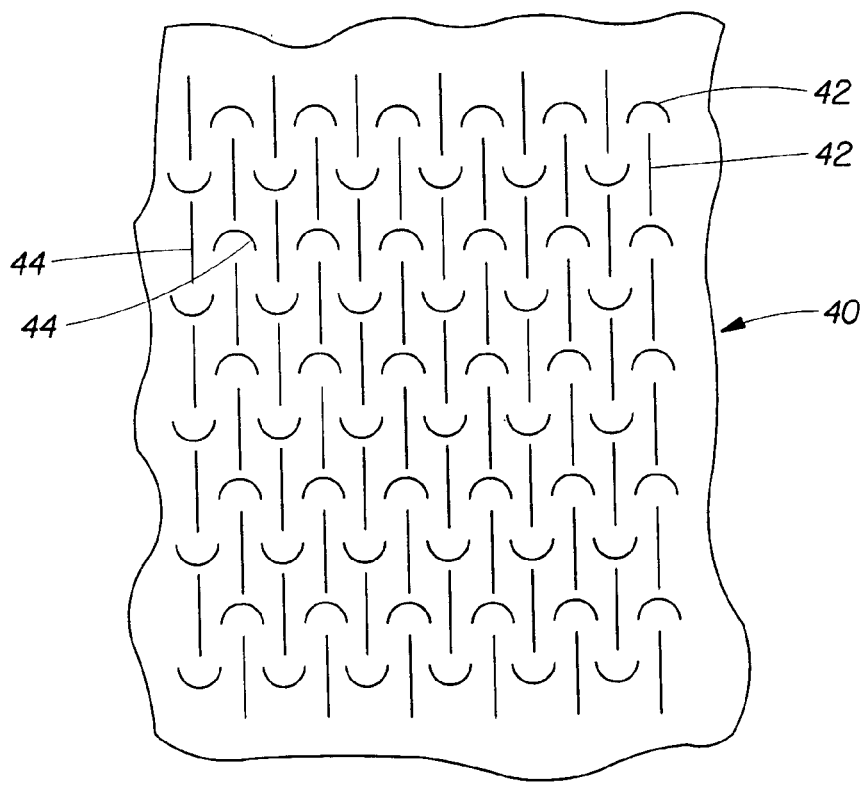
FIG. 29B is a fragmentary top plan view of a tissue paper having straight slits oriented in a first direction and curvilinear slits interposed among the straight slits.

Referring to FIGS. 29A and 29B, two other patterns are illustrated. The pattern in FIG. 29A is activatable in either direction 82 or in direction 84. Activation in direction 84 is expected to provide greater strain without rupture, i.e., achieving peak load, than activation in direction 82. Likewise, referring to FIG. 29B, the pattern comprises both semicircular-shaped lines of weakness 42 and straight, parallel and unilaterally offset lines of weakness 42. Activation perpendicular to the straight and unilaterally offset lines of weakness 42 will also involve a contribution from the semicircularly-shaped lines of weakness 42. However, activation in a direction parallel to the straight lines of weakness 42 will only involve strain contributions from the semicircularly-shaped lines of weakness 42. Accordingly, activation in the direction perpendicular to the straight lines of weakness 42 is expected to allow greater elongation without rupture than activation in the direction parallel to the straight lines of weakness 42. Thus, the embodiments of FIGS. 29A–29B allow the user to select which degree of activation may be utilized, dependent upon the properties desired at the point of use.

One of ordinary skill will recognize that various patterns of the lines of weakness 42 may be intermixed in the same tissue paper 40. For example, a unit cell may be comprised of lines of weakness 42 which are straight, curvilinear, and comprise slits 44, apertures, etc.

Table 2 below, gives the dimensions of the slits 44 and ligaments for six exemplary, nonlimiting embodiments of the present invention. The dimensions are shown in state 1, prior to activation.

TABLE 2

| | L, Slit Length Perpendicular to Activation Direction (cm) | A, Slit Width Taken Parallel to Activation Direction (cm) | D, Distance Between Slits Perpendicular Activation Direction (cm) | W, Distance Between Slits Taken Parallel to Activation Direction (cm) | Figure Number |
|---|---|---|---|---|---|
| Example 1 | 2.0 | 0.06 | 0.19 | 0.24 | 1 |
| Example 2 | 2.0 | 0.06 | 0.19 | 0.24 | 3 |
| Example 3 | 1.0 | 0.06 | 0.19 | 0.24 | 5 |
| Example 4 | 1.0 | approx. 0 | 0.19 | 0.41 | 7 |
| Example 5 | 1.6 | approx. 0 | 0.95 | varies | 9 |
| Example 6 | 1.3 | approx. 0 | 0.16 | 0.32 | 11 |

Referring still to FIGS. 1–12, six tissue papers 40 above according to the present invention are illustrated before and after activation. Prior to activation, the tissue paper 40 has a first thickness as measured in the Z-direction.

The tissue paper 40 also increases in Z-direction thickness in response to the plastic extension. Such increase in Z-direction thickness is contrary to what would be expected under the traditional theory of Poisson effects. Instead, the Z-direction thickness of the sheet increases. The tissue paper 40 does not return to its original thickness upon release of the applied tensile forces. Further, the tissue paper 40 may expand in the Z-direction an amount, or percentage, which is greater than the elongation parallel to the applied tensile forces. Thus, the tissue paper 40 exhibits two-dimensional auxetic properties.

Thus, according to the present invention, a tissue paper 40 which does not suffer from the drawbacks of a Poisson effect is obtained. Upon activation, rather than narrowing in the Z-direction, the tissue paper 40 according to the present invention becomes thicker in the Z-direction. In this manner, a tissue paper 40 having extremely low densities, lower than heretofore obtainable, results.

Table 3 illustrates the effect of activation at four different points on a unit cell of the tissue paper 40 of FIG. 27 on the thickness, the length in the activation direction, the length in the second direction and the volume of a unit cell of the tissue paper 40 described in Table 3. The tissue paper 40 in FIG. 3 had the following dimensions: L=1.0 cm, D=0.2 cm, W=0.4 cm and A=0.02 cm. The length direction of the tissue paper 40 is considered to be parallel to the direction of the applied tensile force. The width direction is considered to be perpendicular to the direction of the applied tensile force.

TABLE 3

| Strain | 0% | 8.9% | 23.8% | 36.9% | 52.4% |
|---|---|---|---|---|---|
| Thickness (measured) | 0.036 cm | 0.373 cm | 0.537 cm | 0.557 cm | 0.570 cm |
| Length (2W + 2A) | 0.84 cm | 0.915 cm | 1.04 cm | 1.15 cm | 1.28 cm |
| Width (L + D) | 1.20 cm | 1.113 cm | 1.03 cm | 0.883 cm | 0.725 cm |
| Volume | 0.036 cm3 | 0.38 cm3 | 0.575 cm3 | 0.566 cm3 | 0.529 cm3 |
| Volume Index | 1.0 | 10.6 | 16.0 | 15.7 | 14.7 |
| Thickness Index | 1.0 | 10.4 | 14.9 | 15.5 | 15.8 |

The foregoing discussion is directed to single ply tissue paper 40 embodiments. Multi-ply tissue paper 40 embodiments are also feasible. In a multi-ply embodiment, the product may be composed of at least two, and up to any reasonable number of, tissue substrates. The tissue substrates forming the multiple plies may be of identical or different material compositions. For example, a three (or more) ply embodiment may be utilized. Such an embodiment may comprise two outboard plies and one or more central ply(ies). The outboard plies may be provided with properties that are soft to the skin of the user, efficacious for scrubbing of surfaces, etc. The central ply(ies) may be provided for strength or to release cleanser or other functional additives upon activation. Further, one or both of the outer plies may comprise tissue paper 40 without lines of weakness 42, as is known in the art.

If a multi-ply embodiment is selected, the plies may be provided with different patterns of lines of weakness 42. For example, the inner ply(ies) may be provided with a pattern that promotes loft and bulk upon activation. The outer plies may be provided with a pattern that is tactily pleasant or efficacious for scrubbing a particular target surface. A multi-ply sheet analysis is illustrated by Table 4 below. A geometry similar to that shown in FIG. 27, having parallel unilaterally offset slits 44 was tested. The slits 44 and tissue paper 40 had the following parameters prior to activation:

| Unit Cell Dimension: | Sheet Dimension: |
|---|---|
| L: 1.65 cm | Length: 18.7 cm |
| A: 0.09 cm | Width: 15.1 cm |

-continued

| Unit Cell Dimension: | Sheet Dimension: |
|---|---|
| D: 0.10 cm | Number of Plies: 5 |
| W: 0.24 cm | |
| dd: 0.033 cm | |

TABLE 4

| Strain | 0% | 49.7% |
|---|---|---|
| CD Length | 18.7 cm | 28 cm |
| Bulk Volume | 46.6 cm3 | 560 cm3 |
| Volume Index | 1 | 12.0 |

Figure 26:
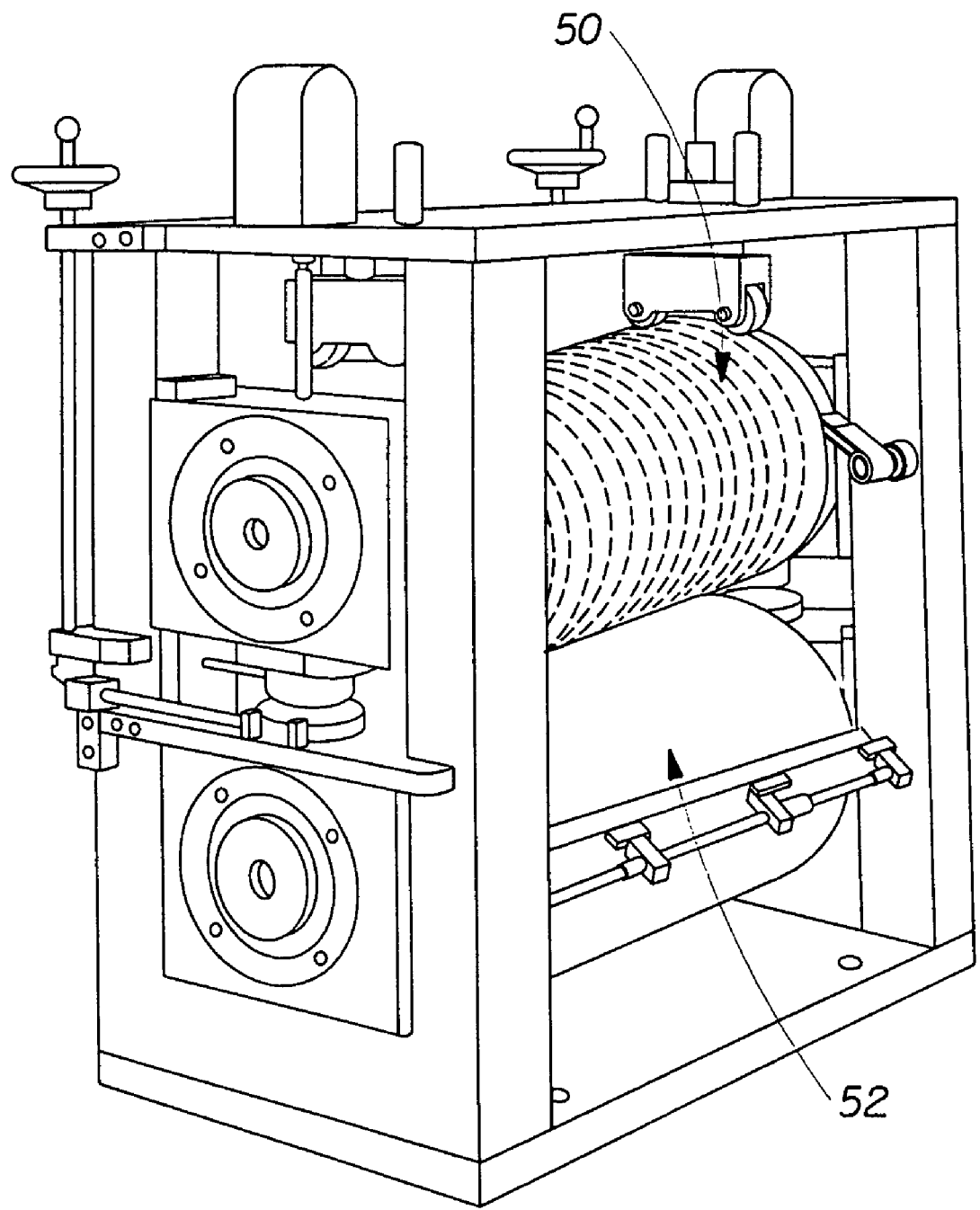
FIG. 26 is a perspective view of a rotary knife which may be utilized to make slits in the tissue of the present invention.

Referring to FIG. 26, the slits 44 or other lines of weakness 42 in the tissue paper 40 may be imparted to the tissue paper 40 in any suitable manner. FIG. 26 illustrates a rotary knife 50 which may be used against a backing roll 52 to impart slits 44 into the tissue paper 40. The pattern of the blades on the rotary knife 50 will correspond to the slits 44 in the tissue. The spaces between the blades will correspond to the lands 48 in the tissue. The tissue is moved relative to the knife, preferably through a nip and the slits 44 may be imparted in a continuous process.

Alternatively, the knife may be flat and stamp the slits 44 into the tissue paper 40. This requires a batch process wherein the slits 44 are stamped into the tissue. Then the tissue paper 40 is moved relative to the stamping knife or, alternatively, a new tissue paper 40 placed under the knife. The knife is then activated stamping the slits 44 and leaving the lands 48 in the patterns as described above.

In yet a more preferred execution, the lines of weakness 42 may comprise low basis weight regions in the tissue paper 40. The tissue paper 40 may have multiple basis weights with higher basis weights providing the lands 48 and the lower basis weights providing the slits 44 or lines of weakness 42.

In a preferred embodiment, the tissue comprises multi-basis weight paper, with the slits 44 as low basis weight regions, or even apertures in a degenerate case. To make multi-basis weight paper, a forming wire having upstanding protuberances is provided. The protuberances may have an aspect ratio of at least 10 in some executions, at least 20 in other executions, and at least 30 in still other executions. The protuberances in the forming wire correspond to the lines of weakness 42 while the spaces between the protuberances correspond to the lands 48. In a particularly preferred process, the high basis weight regions of the tissue paper 40 may have a height, taken perpendicular to the plane of the forming wire less than or slightly greater than that of the protuberances. In a particularly preferred execution, the low basis weight regions will just barely cap over and bridge across the protuberances, leaving a very low basis weight regions which becomes apertures upon activation. This arrangement provides the benefit that the fibers at the edges of apertures will provide softness rather than a rough edge. The softness is believed to be due, in part, to the fiber bonds which rupture upon activation. Rupture of the bonds causes one end of the fibers to remain attached and one to be free, i.e., essentially cantilevered. Such softness is particularly desirable if the activated tissue paper 40 is to be used as an implement for epidermal cleaning as occurs in bath tissue or a body wipe. For a multi-ply product, the fibers at the edges of the slits 44 may lock against the corresponding fibers of adjacent plies. Such locking is believed to help maintain the loft and Z-direction thickness of the product following activation.

Multi-basis weight paper may be made according to any of commonly assigned U.S. Pat. No. 5,245,025, issued Sep. 14, 1993 to Trokhan et al.; U.S. Pat. No. 5,527,428 issued Jun. 18, 1996 to Trokhan et al.; U.S. Pat. No. 5,534,326 issued Jul. 9, 1996 to Trokhan et al.; U.S. Pat. No. 5,654,076, issued Aug. 5, 1997 to Trokhan et al., U.S. Pat. No. 5,820,730, issued Oct. 13, 1998 to Phan et al.; U.S. Pat. No. 5,277,761, issued Jan. 11, 1994 to Phan et al.; U.S. Pat. No. 5,443,691, issued Aug. 22, 1995 to Phan et al.; U.S. Pat. No. 5,804,036 issued Sep. 8, 1998 to Phan et al.; U.S. Pat. No. 5,503,715, issued Apr. 2, 1996 to Trokhan et al.; U.S. Pat. No. 5,614,061, issued Mar. 25, 1997 to Phan et al.; U.S. Pat. No. 5,804,281 issued Sep. 8, 1998 to Phan et al.; U.S. Pat. No. 5,895,623, issued Apr. 20, 1999 to Trokhan et al.; and U.S. Pat. No. 5,900,122 issued May 4, 1999 to Huston, incorporated herein by reference.

Test Methods

The present invention may be characterized as follows. The first characterization uses the elongation occurring at the peak load taken from a load elongation curve. Elongation at peak, also known as strain, is measured in two orthogonal directions. One direction is the activation direction, i.e., the direction of maximum strain without rupture. The other direction is orthogonal thereto. These directions may be coincident with the cross machine and machine directions, respectively. The activation direction, e.g. cross machine direction, bandwidth 70, described below, of the load elongation curve relative to a moving average up to the peak is also determined. Volume and thickness of the product both prior to and following activation is measured to yield a volume index and a thickness index, respectively. The invention may also be characterized by its coefficient of friction and by its flexibilities as measured in the machine direction, cross machine direction, and ratio of the machine and cross machine direction flexibilities.

For each of the tests described below, unless otherwise indicated, a sample is selected and provided. The sample comprises at least one unit cell of the pattern of lines of weakness 42 in the tissue paper 40 and should coincide with one unit as presented to the consumer. If the pattern is closely spaced, so that multiple lines of weakness 42 occur on a single product, one product is provided as the sample. For example, the sample may be a single sheet of bath tissue, a single cleaning implement, etc.

The elongation to peak load measurement is made as follows. The two directions cited above for the sample to be tested are determined.

A tensile tester is used to measure load elongation curve data. The tensile tester jaw size is at least equal to the sample width where width is orthogonal to the direction tested. If the sample is too large for the tensile tester, it may be trimmed to 6 inches (15.24 centimeters) square. If the sample is trimmed to 6 inches (15.24 centimeters), the portion of the sample tested should be representative of the portion of the sample which achieves the greatest Z-directional change when stress is applied in either direction of the XY plane. Tensile tester gauge length is equal to 75% of the length of the sample being tested. The sample is oriented in the first direction, centered in the jaws in both directions and clamped. The cross heads are separated at a constant speed of 20 inches (50.8 centimeters) per minute and the resulting load elongation curve recorded at a sampling frequency of 20 data points per second. The elongation test distance should be great enough such that the sample achieves a peak load.

Recordation may be done using Analysis Presentation Software Version 5.3, available from Thwing-Albert Instrument Company of Philadelphia, Pa. This software records the data as absolute load versus crosshead movement. The absolute load is normalized to grams per centimeter by dividing the load by the initial width of the sample orthogonal to the direction tested. The crosshead movement is converted to a percentage strain by dividing the crosshead movement by the original gauge length and multiplying by 100. The peak stress, or load, is found from the load elongation curve. The elongation corresponding to the peak load is recorded as the resulting strain. This procedure is repeated for the second direction. Five samples are tested in each direction and the results averaged to yield the strain at peak load for that particular direction. The strain ratio, which may be the ratio of the cross machine direction elongation at peak load to the machine direction elongation at peak load, is found by simple division.

Table 5 shown below illustrates the machine direction and cross machine direction strains at peak load for various prior art products and for various embodiments of the present invention. Typically, tissue paper 40 according to the prior art had relatively low strain values in the cross machine direction. This occurs because foreshortening, such as creping, rush transfer, or wet microcontraction, in the manufacturing process typically occurs in the machine direction.

One of skill will recognize that the length and width directions of the slits 44 and/or the length and width directions of the tissue paper 40 need not coincide with the machine and cross machine directions. However, these directions are well known and will be understood by one of ordinary skill and are used for convenience in the examples shown below.

However, in the present invention, the slits 44 may have and typically do have a major axis oriented parallel to the machine direction. Such an orientation of the slits 44 allows for activation in the cross machine direction. This orientation is preferable because it makes inadvertent activation in the machine direction less likely to occur. Inadvertent activation may, for example, occur during dispensing.

As illustrated by Table 5, the tissue paper 40 according to the present invention may have a cross machine direction strain of at least 30%, in some executions at least 60%, in other executions at least 90%, in other executions at least 120%, and in still other executions at least 150%. Likewise, the present invention provides strain ratios approximately an order of magnitude greater than obtainable with the prior art. The strain ratio is the ratio of the strains at peak load in two orthogonal directions. The orthogonal directions may be coincident the machine and cross machine directions. The strain ratio may be at least 2, in the executions at least 4, and in still other executions at least 6.

TABLE 5

|  | % MD Strain to Peak | % CD Strain to Peak | CD Strain to Peak/ MD Strain to Peak Strain Ratio |
|---|---|---|---|
| BATH TISSUE |  |  |  |
| Charmin by P&G | 28.9 | 9.2 | 0.3 |
| Charmin Ultra by P&G | 21.2 | 14.0 | 0.7 |

TABLE 5-continued

|  | % MD Strain to Peak | % CD Strain to Peak | CD Strain to Peak/ MD Strain to Peak Strain Ratio |
|---|---|---|---|
| Cottonelle (Ripples) by K-C | 18.4 | 12.9 | 0.7 |
| Cottonelle (Ripples) Ultrasoft by K-C | 16.6 | 10.0 | 0.6 |
| Quilted Northern by FJ | 17.7 | 9.4 | 0.5 |
| Quilted Northern Ultra by FJ | 23.9 | 8.2 | 0.3 |
| Angel Soft by GP | 14.3 | 7.5 | 0.5 |
| Scott by K-C | 19.8 | 6.0 | 0.3 |
| White Cloud by Paper Products Ltd. | 15.8 | 8.1 | 0.5 |
| TOWELS | | | |
| Bounty by P&G | 20.3 | 14.8 | 0.7 |
| Brawny by FJ | 24.3 | 7.2 | 0.3 |
| Scott Ripples by K-C | 19.3 | 12.7 | 0.7 |
| Viva by K-C | 29.3 | 22.4 | 0.8 |
| FACIAL TISSUE | | | |
| Puffs Regular by P&G | 16.5 | 14.0 | 0.8 |
| Puffs Extra Strength by P&G | 18.9 | 10.7 | 0.6 |
| Kleenex Regular by K-C | 17.2 | 7.2 | 0.4 |
| Kleenex Cold Care by K-C | 16.7 | 7.9 | 0.5 |
| Scotties by K-C | 17.0 | 7.5 | 0.4 |
| WIPES | | | |
| Huggies by K-C | 50.2 | 26.5 | 0.5 |
| Pampers by P&G | 19.2 | 8.9 | 0.5 |
| Cottonelle by K-C | 25.2 | 19.8 | 0.8 |
| Charmin KidFresh - P&G | 22.6 | 11.9 | 0.5 |
| NONWOVEN RAW MATERIALS | | | |
| Carded Topsheet by PGI | 53.8 | 68.8 | 1.3 |
| P11 by BDA | 72.0 | 96.1 | 1.3 |
| SMS Cuff by PGI | 45.7 | 60.7 | 1.3 |
| INVENTION | | | |
| Example 1, Straight, L = 2 cm, A = 0.06 cm | 25.9 | 195.9 | 7.6 |
| Example 2, Straight, L = 2 cm, A = 0.06 cm | 25.1 | 156.6 | 6.2 |
| Example 3, Straight, L = 1 cm, A = 0.06 cm | 23.9 | 67.7 | 2.9 |
| Example 4, Straight, L = 1 cm, A = 0 | 15.7 | 32.3 | 2.1 |
| Example 5, Sine Pattern | 17.8 | 77.7 | 4.4 |
| Example 6, Chevron Pattern | 20.6 | 127.9 | 6.2 |

Referring to FIGS. 13A–18, several representative load elongation curves according to the prior art and present invention are illustrated. The load elongation curves show how much greater elongation is obtainable with the present invention, at a lesser peak loading value, than is obtainable with the prior art.

A second parameter, bandwidth 70 is measured as follows. The aforementioned load elongation curve up to the peak load is smoothed using a rolling average technique. The first 3% of strain is omitted to eliminate noise. Every three consecutive data points are averaged together to smooth the curve, such that the moving average at a given datum point is equal to the average of the points immediately preceding and following that datum point.

Referring to FIGS. 19–24, the magnitude of the deviation, expressed as a percent of the peak load above and below the smoothed curve, is found for each datum point by subtracting the load from the rolling average and dividing by the peak load. In FIGS. 19–24, the X-axis represents the rolling average curve. All points greater than (above on the graph) the rolling average are again averaged together to yield the upper limit of the bandwidth 70. Likewise, all points less than (below on the graph) the rolling average are averaged together to give the lower limit of the bandwidth 70. The bandwidth 70 is defined as the sum of the absolute values of the upper and lower limits.

Excel software, available from Microsoft Corporation of Redmond, Wash., or any other spreadsheet, as well known to one of ordinary skill, may be utilized. As illustrated in Table 6 below, the data points taken from the load elongation curve may be plotted in columnar form. The first column provides the strain at each datum point. For tissue papers 40 according to the present invention, the entire load elongation curve may yield 200 or more data points for the prior art and 1,200 individual data points or more for the present invention. However, only data points up to the peak load are considered. Therefore, n data points are utilized with n being on the order of 200 or more. It is to be noted that the prior art samples typically exhibited fewer total data points, on the order of 20 or more.

The first column in Table 6 is the strain. It is to be noted that Table 6 below ends when the nth data point on the load column equals the peak data point on the load elongation curve. The second column is the load corresponding to each strain in the first column. The third column is the rolling average of the load found at each three consecutive data points in the second column. For each point on the strain curve, the rolling average considers the data points immediately before and immediately after a particular point on the strain curve. The fourth column represents the deviation of the load at any particular data point from the rolling average. Such deviation is found by subtracting the value of the second column from the value of the third column and dividing that difference by the peak load in the second column. The fifth column represents all of the positive values taken from the fourth column. These values are averaged together to yield the upper limit of the bandwidth 70. The sixth column represents all of the negative values taken from the fourth column. These values are averaged together to yield the lower limit of the bandwidth 70.

TABLE 6

| X Axis Strain | Y Axis Load | Average of 3 Data Points For Load | Percent Deviation of Load: (Column 3– Column 2)/$Y_n$ | Positive Deviations from Column 4 | Negative Deviations from Column 4 |
|---|---|---|---|---|---|
| $X_1$ | $Y_1$ | — | — | — | — |
| $X_2$ | $Y_2$ | Average $Y_2$ | $Deviation_2$ | Positive $Deviation_2$ | — |
| $X_3$ | $Y_3$ | Average $Y_3$ | $Deviation_3$ | — | Negative $Deviation_3$ |
| $X_{n-1}$ | $Y_{n-1}$ | $Average_{n-1}$ | $Deviation_{n-1}$ | Positive $Deviation_{n-1}$ | — |
| $X_n$ | $Y_n$, peak load | — | — | Average of Positive Deviations, Upper Limit of Bandwidth | Average of Negative Deviations, Lower Limit of Bandwidth |

Referring to FIGS. 19–25, the smoothed load elongation curve may be plotted using the rolling average as a straight and horizontal line. The deviation expressed as a percent relative to peak load from the rolling average is plotted, as are the upper and lower limits of the band width.

As can be seen from Table 7 below, the prior art typically displays a bandwidth 70 considerably less than that of the present invention. Preferably, the present invention in some executions has a bandwidth 70 at least 0.5, in other executions at least 0.7, and in other executions at least 0.9. It is believed that the relatively large bandwidth 70 of the present invention is due to the incremental fracturing of ligaments, and consequently, lesser load carrying capability which occurs as large lands 48 (rather than individual fibers) are fractured.

TABLE 7

|  | Bandwidth % |
|---|---|
| BATH TISSUE | |
| Charmin LDT | 0.32 |
| Charmin Ultra | 0.37 |
| Cottonelle (KC Ripples) | 0.32 |
| Cottonelle (KC Ripples) Ultrasoft | 0.33 |
| White Cloud by Paper Products Ltd. | 0.31 |
| TOWELS | |
| Bounty | 0.03 |
| FACIAL TISSUE | |
| Puffs Regular | 0.22 |
| WIPES | |
| Pampers | 0.37 |
| NONWOVEN RAW MATERIALS | |
| P11 | 0.28 |
| INVENTION | |
| Example 1 | 0.75 |
| Example 2 | 1.31 |
| Example 3 | 0.45 |
| Example 4 | 0.87 |
| Example 5 | 1.45 |
| Example 6 | 2.23 |

Z-direction thickness and sample volume are measured as follows. An unactivated sample to be examined is placed on a flat, horizontal reference surface. The tissue paper 40 is denoted with the largest inscribed square. A flat square Type 302 stainless steel platen 60 having a thickness of 0.015 inches (0.0381 centimeters) is provided. The platen 60 has a size and area ⅑ that of the aforementioned inscribed square. By sizing the platen 60 relative to the inscribed square of the sample, a measure corresponding to various sized products is obtainable.

Figure 28:
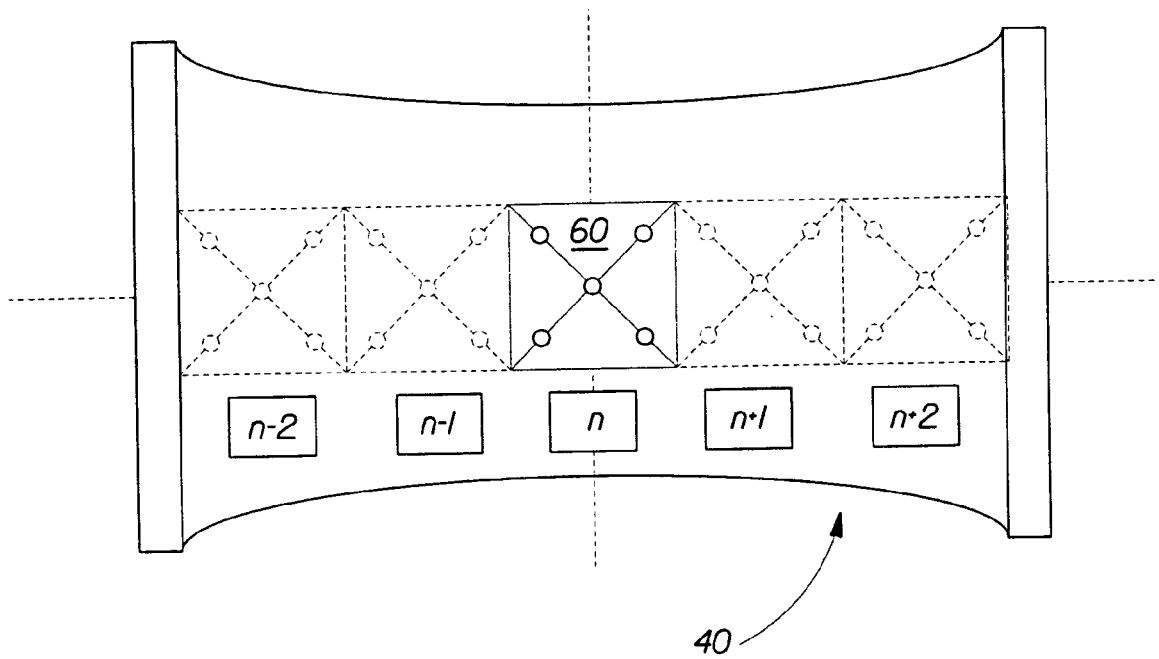
FIG. 28 is a schematic top plan view of a tissue paper and platen showing how the thickness measurement is conducted.

Referring to FIG. 28, the center of the platen 60 is found. The platen 60 is marked with diagonals, intersecting at the center, and extending to each corner of the platen 60. The diagonals are marked at positions ⅔ of distance from the center to each corner and at the center for a total of five positions. These five positions indicate the measuring points for subsequent thickness measurements.

The stainless steel platen 60 is laid upon the reference surface and zeroed for its own tare thickness using a Digimatic Height Gauge, Model No. HDS-8"M made by the Mitutoyo Corporation of Japan. The stylus tip of the height gauge is dropped to the point of contact with the platen 60 as it rests upon the sample. The platen 60 is tested for flatness by zeroing the gauge on the center of the platen 60.

The platen 60 is flat if all other indicated measuring points are +/−0.01" (0.254 millimeters). The sample is placed on the reference surface and oriented such that the direction of greatest % strain before failure is left/right to the observer.

Referring to FIG. 28, the sample is fastened to the reference surface on the far left and far right edges using adhesive tape along the full width of the sample. The adhesive tape should secure 12.5% of the total length of the sample on both the right and the left sides, leaving the middle 75% of the sample as gauge length for analysis. The platen 60 should be carefully placed on top of the sample so as not to disturb the sample. The platen 60 is centered on the sample with the edges of the platen 60 aligned with the aforementioned first and second directions. The height of the platen 60, representing the thickness of the sample when the tare is accounted for, is measured at each of the indicated five points on the platen 60. The average height of the five readings is recorded at this platen 60 position and represents the Z-direction thickness at this position of the platen 60.

While the platen 60 is in each position, the average width at each side of the platen 60 of the sample for this segment (perpendicular to the direction of increment of the platen 60) is also measured. Finally, the length of the sample is determined. The length is equal to the length of the side of the measuring platen 60. The length and width of the sample may be measured to a resolution of 1.6 millimeters using an ordinary scale available from The Starrett Company of Athol, Mass.

The platen 60 is moved one full position to the left (or right) of its original position to position n+1. The height of the five points and length and width of the segment are again measured. The platen 60 is again moved one full position to the left (or right) and the five points remeasured and averaged. This procedure continues until the edge of the sample is reached. The thickness of the sample outboard of and perpendicular to the direction of increments of the platen 60 is not measured. The portion of the sample secured with adhesive tape is not measured. At the edge of the sample, only points on the platen 60 lying inside of the sample are considered. For the edges, the length of the segment may not be equal to the length of one side of the platen 60. If the platen 60 overhangs the sample, any points lying outside of the sample are not considered for the height measurement. The platen 60 is then returned to one position to the right (or left) of the center position at position n−1 and the procedure repeated until the opposite edge of the sample is reached. The height measurements at each position are averaged to yield one height for each position of the platen 60.

At each position of the platen 60, the height, width and length are multiplied together. Thus, a volume for each incremental position of the platen 60 is found. These volumes at the incremental positions are summed together to yield a final volume for the sample.

The sample is then activated in tension. First, the adhesive tape securing the sample is removed and the sample is clamped along the full width of the sample (again 12.5% on the far left and far right of the figure). The sample is then activated in tension by moving the clamps apart at 50.8 centimeters per minute. To find the proper strain, the aforementioned load elongation curve is used. Elongation is measured in the activation direction which normally occurs during use of the product according to the present invention.

The gauge length of the sample is elongated in tension to 75% of the strain required to reach the peak value noted above. This elongation is referred to as the 75% peak elongation. Failure in tensile loading does not occur. The gauge length of the sample is relaxed from the 75% peak elongation to a 67% peak elongation. If relaxation does not occur due to the inherent spring forces in the product, relaxation may be manually induced. The sample is then carefully held in place on a horizontal reference surface at the 67% peak elongation using adhesive tape as appropriate. The volume measurement is repeated as described above.

Three samples are tested in each state. The three state 1 volumes are averaged. The three state 2 volumes are averaged. The volume index may be considered as the state 2 average volume divided by the state 1 average volume. The volume index represents the change in volume of the elongated portion of the sample.

The thickness index is found as follows. The maximum thickness at any platen 60 position is found in state 1 for each of three samples. The thickness data from the volume measurement above can be used or a new thickness measurement can be taken. The maximum thickness at any platen 60 position is found for each of the three activated samples. These maximum values are then ratioed for each of the three samples. The three ratios are then averaged together to give a thickness index representative of that product, based upon the three samples.

Referring to Table 8 below, it can be seen that products according to the prior art do not noticeably activate or change intensive properties upon application of tensile forces. Accordingly, the volume index is approximately equal to one for the prior art samples. The present invention may have a volume index of at least 5, in other executions at least 10, in other executions at least 15, in other executions at least 20, and in other executions at least 25.

Referring still to Table 8 below, the state 1 and state 2 average thicknesses are the averages represented by summing the thickness and area for each platen 60 position divided by the summation of the areas for each platen 60 position. This may be conceptually thought of as a weighted average of the volume divided by the area at each platen 60 position. Again, an average of three samples is represented for each of the state 1 and state 2 thicknesses.

The state 1 and state 2 maximum thicknesses are the average of the maximum thicknesses of three identical samples in each state. However, it is to be recognized that to determine the thickness index, three thickness indices, one for each sample, are found as described above and then averaged.

The tissue paper 40 according to the present invention may have a thickness index of at least 2, in some executions at least 4, in some executions at least 6, in some executions at least 8, in some executions at least 10, and in still other executions at least 12.

TABLE 8

| | State 1 Volume based on 14.6 × 15.2 cm Sample (cc) | State 2 Volume (cc) | Volume Index (unitless) | State 1 Average Thickness (cm) | State 2 Average Thickness (cm) | State 1 Max. Thickness (cm) | State 2 Max. Thickness (cm) | Thickness Index (unitless) |
|---|---|---|---|---|---|---|---|---|
| BATH TISSUE | | | | | | | | |
| Quilted Northern Ultra | 23.4 | 23.41 | ~1 | 0.106 | ~0.106 | 0.11 | ~0.11 | ~1 |
| TOWELS | | | | | | | | |
| Brawny | 27.1 | 27.1 | ~1 | 0.122 | ~0.122 | 0.14 | ~0.14 | ~1 |
| FACIAL TISSUE | | | | | | | | |
| Kleenex Cold Care | 20.3 | 20.31 | ~1 | 0.091 | ~0.091 | 0.15 | ~0.15 | ~1 |
| WIPES | | | | | | | | |
| Huggies | 27.3 | 27.3 | ~1 | 0.123 | ~0.123 | 0.14 | ~0.14 | ~1 |
| INVENTION | | | | | | | | |
| Example 1 | 45.2 | 565.0 | 12.5 | 0.203 | 1.77 | 0.21 | 2.45 | 11.5 |
| Example 2 | 48.9 | 357.5 | 7.3 | 0.220 | 1.24 | 0.24 | 1.53 | 6.5 |
| Example 3 | 44.4 | 280.2 | 6.3 | 0.199 | 1.36 | 0.22 | 1.45 | 6.7 |
| Example 4 | 30.1 | 250.5 | 8.3 | 0.135 | 1.14 | 0.14 | 1.24 | 8.6 |
| Example 5 | 55.4 | 354.9 | 6.4 | 0.249 | 1.37 | 0.26 | 1.55 | 6.0 |
| Example 6 | 48.4 | 311.0 | 6.4 | 0.218 | 1.16 | 0.22 | 1.41 | 6.3 |

The thickness of the tissue paper 40 according to the present invention is dependent upon the number of plies. For the embodiments described and claimed herein, embodiments having one, two or n plies, with n being an integer number between about 2 and about 8, and in some executions between 4 and 6, have been found suitable. For the multi-ply embodiments described and claimed herein, the tissue paper 40 according to the present invention may have a State 2 thickness at any position, measured as described above, of at least about 0.5 centimeters, in some executions about 1 centimeters, in other executions at least about 1.3 centimeters, in other executions at least about 1.5 centimeters, and in still other execution at least about 1.7 centimeters. For single-ply embodiments, the thickness may be at least about 0.3 centimeters, in other executions at least about 0.4 centimeters, in still other executions at least about 0.5 centimeters, and in still other executions at least about 0.6 centimeters. Generally, as the perpendicular distance between lines of weakness W increases, the thickness of the tissue paper 40 likewise increase. It will be understood by one of ordinary skill that the slit length must be great enough to accommodate the increase in thickness as the land areas W tend to deform out of the plane of the tissue paper 40 upon activation.

Furthermore, the tissue paper 40 according to the present invention has a lower density following activation than is found in the prior art. To measure the density of the tissue under consideration, the following procedure is used. The volume of the tissue is determined as set forth above. The mass of the tissue is determined, in grams, using a digital balance. A suitable balance has a resolution of 0.0001 g and is available from The Sartorius Company, Goettingen, Del. Density is simply the mass of the sample divided by the volume. Referring to Table 9, the density of various products according to the prior art, and according to the claimed invention, are illustrated. Upon activation, the product according to the present invention has a density which is approximately an order of magnitude less than that of the prior art. The product according to the present invention is particularly advantageous when used as a low density substrate for bath tissue, facial tissue, a hard surface cleaner, etc.

TABLE 9

|  | Density (g/cm³) |
|---|---|
| BATH TISSUE |  |
| Quilted Northern | 0.0408 |
| TOWELS |  |
| Brawny | 0.0411 |
| FACIAL TISSUE |  |
| Kleenex Cold Care | 0.0444 |
| WIPES |  |
| Huggies | 0.248 |
| INVENTION |  |
| Example 1 (post activation) | 0.0044 |
| Example 2 (post activation) | 0.0072 |
| Example 3 (post activation) | 0.0091 |
| Example 4 (post activation) | 0.0074 |
| Example 5 (post activation) | 0.0054 |
| Example 6 (post activation) | 0.0061 |

As can be seen from Table 9 above, the present invention may have a density of less than 0.01, in some executions less than 0.009, in other executions less than 0.008, in other executions less than 0.007, and in still other executions less than 0.006 g/cm³.

Figure 30A:
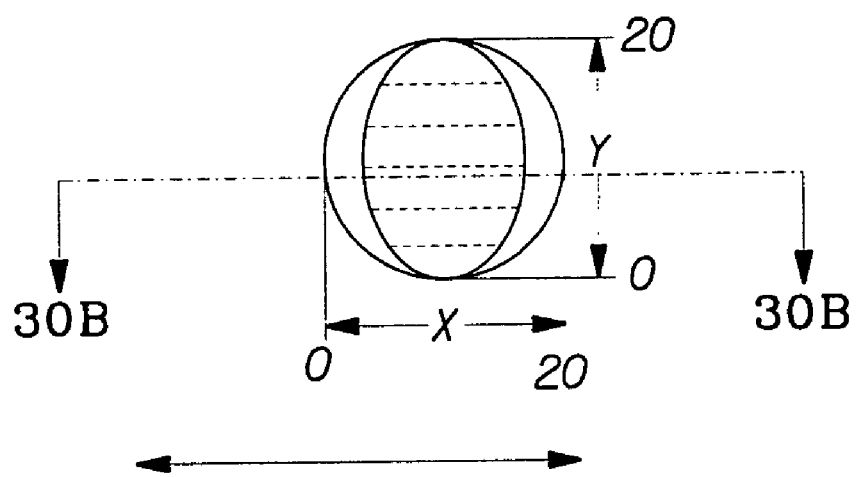
FIG. 30A is a schematic bottom plan view of the probe used in the coefficient of friction test method.
Figure 30B:
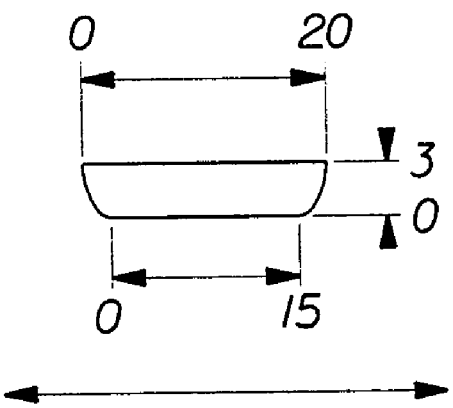
FIG. 30B is a vertical sectional view of the probe of FIG. 30A taken along lines 30B—30B.

Referring to yet another parameter, the present invention also has a relatively high coefficient of friction upon activation. The average coefficient of friction is the average of the coefficients of friction measured in the machine and cross machine directions. The coefficient of friction is measured using a Kawabata Evaluation System (KES) testing machine available from Kato Tech Co. Ltd. The sample is secured on a horizontal reference surface. A probe and arm having a weight of approximately 12.2 grams made of sintered glass is used. The probe is sintered glass having a diameter of 20 millimeters and porocity C is available from Ace Glass, Inc. of Vineland, N.J. under catalog number 7176-14. Referring to FIGS. 30A–30B, the probe is modified to chamfer the edges. The edges of the bottom circumference of the probe are chamfered using 100 grit sandpaper. K224 100-J sandpaper from Norton Abrasives has been found suitable. The probe is drug along the sample at a speed of 0.1 centimeters per minute for a distance of 2.0 centimeters. The direction of the probe is reversed, for a bilateral test pattern. A different sample is provided. This sample is oriented at 90 degrees to the first sample and the test repeated. The forward and backward traces at each orientation (four data points) are averaged to yield the coefficient of friction for that sample. The average of three such samples yields the coefficient of friction for the tissue paper 40. As illustrated in Table 10 below, the present invention upon activation has a coefficient of friction of at least 1.8, in some executions greater than 2.0, in other executions greater than 2.2, and in still other executions greater than 2.4.

TABLE 10

|  | Avg. COF |
|---|---|
| BATH TISSUE |  |
| Charmin LDT | 0.84 |
| Charmin Ultra | 0.76 |
| Cottonelle (KC Ripples) | 0.61 |
| Cottonelle (KC Ripples) Ultrasoft | 0.63 |
| Quilted Northern | 0.68 |
| Quilted Northern Ultra | 0.77 |
| Angel Soft | 0.92 |
| Scott | 0.79 |
| White Cloud by Paper Products Ltd. | 0.92 |
| TOWELS |  |
| Bounty | 0.68 |
| Brawny | 0.53 |
| Scott Ripples | 0.81 |
| Viva | 0.89 |
| FACIAL TISSUE |  |
| Puffs Regular | 0.61 |
| Puffs Extra Strength | 0.65 |
| Kleenex Regular |  |
| Kleenex Cold Care | 0.43 |
| Scotties | 0.46 |
| WIPES |  |
| Huggies | 1.07 |
| Pampers | 1.84 |
| Cottonelle | 1.51 |
| Charmin KidFresh | 1.48 |
| INVENTION |  |
| Example 1, State 1/State 2 | 1.1/2.3 |
| Example 2, State 1/State 2 | 1.3/2.5 |
| Example 3, State 1/State 2 | 0.9/2.1 |
| Example 4, State 1/State 2 | 0.5/1.5 |
| Example 5, State 1/State 2 | 0.6/1.8 |
| Example 6, State 1/State 2 | 0.7/1.8 |

The stiffness of the sample may be measured using a cantilever drape tester adapted from ASTM B1388-64. A sample has a width of 2.54 centimeters and a length sufficient to allow a drape of 45° from the horizontal to occur. A length of 10.16 cm for tissue and 15.24 cm for paper towel has been found satisfactory. The sample has the long axis parallel to either machine or cross machine directions. The basis weight of the sample in pounds per 3000 square feet is determined using techniques well known to one of ordinary skill and which will not be repeated herein. The sample is placed on a horizontal test platform having a 90° free corner to allow overhang of the sample to occur. The sample is moved over the free edge at a rate of ½ inches (1.27 centimeters) per second until the overhang portion of the sample drapes 45° from the horizontal. The overhang length of the sample is measured to the nearest 0.5 centimeters.

The thickness of the sample is measured as described above. The bending modulus is then found according to the formula Bending Modulus (kg/cm²)={(overhang length (cm)/ 2)³×Basis Weight (pounds/3000 sq. ft.)×119.24}/ [thickness (thousands of inches or mils)]³

As can be seen from Table 11 below, the present invention has a cross machine direction bending modulus approximately in order of magnitude less than obtainable with the prior art. The present invention may have a cross machine direction bending modulus less than 0.01 kg/cm², less than 0.005 kg/cm², in some executions less than 0.001 kg/cm², and in some executions less than 0.0005 kg/cm², in some executions less than 0.0001 kg/cm², and in some executions less than 0.00005 kg/cm². However, the machine direction to cross machine direction bending modulus ratio is approximately an order of magnitude greater than that obtainable by the prior art. The machine direction to cross machine direction bending modulus ratio may be at least about 5 in some executions, at least about 10 in some executions, at least about 15 in other executions, and at least about 20 in other executions.

TABLE 11

|  | MD Bending Modulus kg/cm² | CD Bending Modulus kg/cm² | MD/CD Bending Modulus (unitless) |
|---|---|---|---|
| BATH TISSUE |  |  |  |
| Quilted Northern Ultra | 0.3 | 0.4 | 0.8 |
| TOWELS |  |  |  |
| Brawny | 4.2 | 7.9 | 0.5 |
| FACIAL TISSUE |  |  |  |
| Kleenex Cold Care | 0.1 | 0.3 | 0.3 |
| WIPES |  |  |  |
| Huggies | 0.5 | 1.0 | 0.5 |
| INVENTION |  |  |  |
| Example 1, State 1/State 2 | 0.7/0.00041 | 0.04/0.00002 | 17.5/20.5 |
| Example 2, State 1/State 2 | 0.4/0.00089 | 0.1/0.00004 | 4.0/22.3 |
| Example 3, State 1/State 2 | 0.4/0.00111 | 0.2/0.00047 | 2.0/2.4 |
| Example 4, State 1/State 2 | 2.5/0.00191 | 0.8/0.00039 | 3.1/4.9 |
| Example 5, State 1/State 2 | 0.3/0.00052 | 0.1/0.00006 | 3.0/8.7 |
| Example 6, State 1/State 2 | 0.3/0.00087 | 0.1/0.00005 | 3.0/17.4 |

The state 1/state 2 MD bending modulus and CD bending modulus ratios are also illustrated in Table VIB below. As illustrated by Table 12, state 1/state 2 CD flexibility ratios of at least 4, and some executions at least 5, and in other executions at least 6 are obtainable.

TABLE 12

|  | State 1/State 2 Ratio of Bending Modulus MD | State 1/State 2 Ratio of Bending Modulus CD |
|---|---|---|
| Example 1 | 1707 | 2000 |
| Example 2 | 449 | 2500 |
| Example 3 | 360 | 426 |
| Example 4 | 1309 | 2051 |
| Example 5 | 577 | 1667 |
| Example 6 | 345 | 2000 |

What is claimed is:

1. A generally planar substrate of tissue paper, said substrate having a length direction and a width direction defining an XY plane and a Z-direction perpendicular thereto,
    said substrate having a thickness taken in the Z-direction, said substrate being extensible in at least one of said length direction and said width direction, whereby plastic extension of said substrate to a percentage in either said length direction or said width direction of said XY plane yields a percentage increase in thickness greater than said percentage elongation in said XY plane.

2. A substrate according to claim 1 wherein said substrate has apertures therethrough prior to said plastic extension.

3. A substrate according to claim 2 wherein said apertures are elongate.

4. A substrate according to claim 3 wherein said elongate apertures are generally parallel.

5. A substrate according to claim 4 wherein said elongate apertures are unilaterally offset from adjacent apertures.

6. A multi-ply tissue product, said tissue product defining an XY plane and a Z-direction perpendicular thereto, said tissue product having a thickness of at least 2 mm and a density of less than 0.01 g/cm³.

7. A tissue product according to claim 6, having a machine direction and a cross machine direction orthogonal thereto, said tissue product having a cross machine direction flexibility of less than 0.0 kg/cm².

8. A tissue paper, said tissue paper having a first thickness, said tissue paper being plastically activatable in tension whereby said tissue has a second thickness upon activation, the ratio of said second thickness to said first thickness defining a thickness index, said thickness index is at least 4.

9. A tissue paper according to claim 8, wherein said tissue comprises cellulosic fibers.

10. A tissue paper according to claim 8, wherein said tissue comprises synthetic fibers.

11. A tissue paper according to claim 9, wherein said thickness index is at least 6.

12. A tissue paper according to claim 8, wherein said thickness index is at least 10.

13. A tissue paper according to claim 11, having a machine direction and a cross machine direction orthogonal thereto, said tissue paper having an elongation in said cross machine direction of at least 30% without rupture.

14. A tissue paper according to claim 13, wherein said tissue paper has an elongation in the cross machine direction of at least 60% without rupture.

15. A generally planar tissue paper comprising at least two plies joined in face-to-face relationship, wherein at least one of the plies comprises the substrate according to claim 1, said tissue paper having a length direction and a width direction defining an XY plane and a Z-direction perpendicular thereto, said tissue paper having a thickness in said Z-direction, said tissue paper being plastically extensible in at least one of said length direction and said width direction, whereby plastic extension of said tissue paper causes an increase in said thickness of said tissue paper.

16. A tissue paper according to claim 15, comprising at least three plies joined in face-to-face relationship, two outboard plies and at least one center ply therebetween, each of said plies comprising a tissue paper substrate having a pattern of lines of weakness therein, said pattern of lines of weakness of said center ply being different than said pattern of lines of weakness of at least one of said outboard plies.

17. A multi-ply tissue paper comprising apertures therethrough, said multi-ply tissue paper having a coefficient of friction of at least 2.2.

18. A tissue paper according to claim 17, wherein said tissue paper is activatable from a first state to a second state yielding a load elongation curve, said load elongation curve having a bandwidth of at least about 0.5.

19. A tissue paper according to claim 18, wherein said bandwidth is at least about 0.9.

20. A tissue paper comprising the substrate according to claim 1, and having a basis weight of 10 to 140 grams per square meter, said tissue paper having a plurality of lines of weakness therein, said tissue paper being activatable in a first direction, whereby opposed tensile forces cause strain in said tissue paper parallel to said direction of opposed tensile forces, said thickness of said tissue paper increasing in response to said strain.

21. A tissue paper according to claim 20, wherein said tissue paper may be elongated to a predetermined strain without reaching a peak load on a load elongation curve in either of two orthogonal directions, said strain in said first direction being at least twice as great as said strain in said second direction.

* * * * *